(12) United States Patent
Yoshida et al.

(10) Patent No.: US 9,095,662 B2
(45) Date of Patent: *Aug. 4, 2015

(54) BLOOD STORAGE BAG SYSTEM AND DEPLETION DEVICES WITH OXYGEN AND CARBON DIOXIDE DEPLETION CAPABILITIES

(71) Applicant: New Health Sciences, Inc., Bethesda, MD (US)

(72) Inventors: Tatsuro Yoshida, West Newton, MA (US); Paul J Vernucci, Billerica, MA (US)

(73) Assignee: New Health Sciences, Inc., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/969,095

(22) Filed: Aug. 16, 2013

(65) Prior Publication Data

US 2013/0333561 A1   Dec. 19, 2013

Related U.S. Application Data

(63) Continuation of application No. 12/901,350, filed on Oct. 8, 2010, now Pat. No. 8,535,421.

(60) Provisional application No. 61/331,693, filed on May 5, 2010, provisional application No. 61/250,661, filed on Oct. 12, 2009.

(51) Int. Cl.
*B01D 53/22* (2006.01)
*B01D 19/00* (2006.01)
(Continued)

(52) U.S. Cl.
CPC ............ *A61M 1/342* (2013.01); *A61M 1/0209* (2013.01); *A61M 1/0218* (2014.02);
(Continued)

(58) Field of Classification Search
CPC ........ B01D 53/22; B01D 19/00; B01D 53/04; B01D 63/02; B01D 2215/00; B01D 2257/104; B01D 2311/13; B01D 2313/40; B01D 2311/2626; B01D 19/0031; A61M 1/0209; A61M 1/0272; A61M 2001/0231; A61M 2202/0208; A61M 1/342; A61M 1/0218; A61M 1/0231; A61M 2202/0225
USPC ................ 95/46, 51, 54; 96/4, 6, 8; 604/4.01, 604/5.01, 5.04, 6.01, 6.15; 435/2; 206/524.6
See application file for complete search history.

(56) References Cited

U.S. PATENT DOCUMENTS 3,668,837 A  *   6/1972  Gross .................................. 96/6
3,910,841 A  *  10/1975  Esmond ......................... 210/231
(Continued)

FOREIGN PATENT DOCUMENTS

CN   2894710 Y   5/2007
DE   3722984     1/1989
(Continued)

OTHER PUBLICATIONS

Alcantar et al., "Polyethylene glycol-coated biocompatible surfaces," *Journal of Biomedical Materials Research*, 51(3):343-351 (2000).
(Continued)

*Primary Examiner* — Jason M Greene
(74) *Attorney, Agent, or Firm* — Arnold & Porter LLP

(57) ABSTRACT

A blood storage system. The system has a collection bag for red blood cells; an oxygen/carbon dioxide depletion device; a storage bag for red blood cells; and tubing connecting the collection bag to the depletion device and the depletion device to the storage bag. The depletion device includes a receptacle of a solid material having an inlet and an outlet adapted to receiving and expelling a flushing gas; a plurality of hollow fibers or gas-permeable films extending within the receptacle from an entrance to an exit thereof. The hollow fibers or gas-permeable films are adapted to receiving and conveying red blood cells.

8 Claims, 14 Drawing Sheets

(51) Int. Cl.
  *A61M 1/34* (2006.01)
  *A61M 1/02* (2006.01)
(52) U.S. Cl.
  CPC .......... *A61M 1/0231* (2014.02); *A61M 1/0272* (2013.01); *B01D 19/0031* (2013.01); *B01D 53/22* (2013.01); *A61M 2202/0208* (2013.01); *A61M 2202/0225* (2013.01)

(56) References Cited

U.S. PATENT DOCUMENTS

| | | | |
|---|---|---|---|
| 4,086,924 A | 5/1978 | Latham, Jr. | |
| 4,225,439 A * | 9/1980 | Spranger | 210/321.89 |
| 4,228,032 A | 10/1980 | Talcott | |
| 4,300,559 A | 11/1981 | Gajewski et al. | |
| 4,342,723 A * | 8/1982 | Sado et al. | 96/6 |
| 4,370,160 A | 1/1983 | Ziemelis | |
| 4,381,775 A | 5/1983 | Nose' et al. | |
| 4,540,416 A | 9/1985 | Hattori et al. | |
| 4,572,899 A | 2/1986 | Walker et al. | |
| 4,585,735 A | 4/1986 | Meryman et al. | |
| 4,654,053 A | 3/1987 | Sievers et al. | |
| 4,670,013 A | 6/1987 | Barnes et al. | |
| 4,701,267 A | 10/1987 | Watanabe et al. | |
| 4,713,176 A | 12/1987 | Schoendorfer et al. | |
| 4,748,121 A | 5/1988 | Beaver et al. | |
| 4,769,175 A | 9/1988 | Inoue | |
| 4,769,318 A | 9/1988 | Hamasaki et al. | |
| 4,837,047 A | 6/1989 | Sato et al. | |
| 4,880,548 A | 11/1989 | Pall et al. | |
| 4,880,786 A | 11/1989 | Sasakawa et al. | |
| 4,902,701 A | 2/1990 | Batchelor et al. | |
| 4,925,572 A | 5/1990 | Pall | |
| 5,000,848 A | 3/1991 | Hodgins et al. | |
| 5,023,054 A | 6/1991 | Sato et al. | |
| 5,037,419 A | 8/1991 | Valentine et al. | |
| 5,152,905 A | 10/1992 | Pall et al. | |
| 5,208,335 A | 5/1993 | Ramprasad et al. | |
| 5,229,012 A | 7/1993 | Pall et al. | |
| 5,254,248 A | 10/1993 | Nakamura et al. | |
| 5,353,793 A | 10/1994 | Bornn | |
| 5,356,375 A | 10/1994 | Higley | |
| 5,362,442 A | 11/1994 | Kent | |
| 5,386,014 A | 1/1995 | Nho et al. | |
| 5,387,624 A | 2/1995 | Morita et al. | |
| 5,417,986 A | 5/1995 | Reid et al. | |
| 5,427,663 A | 6/1995 | Austin et al. | |
| 5,443,743 A | 8/1995 | Gsell | |
| 5,476,764 A | 12/1995 | Bitensky | |
| 5,506,141 A | 4/1996 | Weinreb et al. | |
| 5,529,821 A | 6/1996 | Ishikawa et al. | |
| 5,617,873 A | 4/1997 | Yost et al. | |
| 5,624,794 A | 4/1997 | Bitensky et al. | |
| 5,635,358 A | 6/1997 | Wilding et al. | |
| 5,691,452 A | 11/1997 | Gawryl et al. | |
| 5,693,230 A | 12/1997 | Asher | |
| 5,698,250 A | 12/1997 | DelDuca et al. | |
| 5,730,989 A | 3/1998 | Wright | |
| 5,750,115 A | 5/1998 | Van Den Bosch | |
| 5,783,094 A | 7/1998 | Kraus et al. | |
| 5,783,148 A | 7/1998 | Cottingham et al. | |
| 5,789,151 A | 8/1998 | Bitensky et al. | |
| 5,811,142 A | 9/1998 | DelDuca et al. | |
| 5,846,427 A | 12/1998 | Kessler et al. | |
| 5,902,747 A | 5/1999 | Nemser et al. | |
| 5,972,710 A | 10/1999 | Weigl et al. | |
| 6,027,623 A | 2/2000 | Ohkawa | |
| 6,045,701 A | 4/2000 | Ung-Chhun et al. | |
| 6,047,203 A | 4/2000 | Sackner et al. | |
| 6,090,062 A | 7/2000 | Sood et al. | |
| 6,150,085 A | 11/2000 | Hess et al. | |
| 6,162,396 A | 12/2000 | Bitensky et al. | |
| 6,187,572 B1 | 2/2001 | Platz et al. | |
| 6,210,601 B1 | 4/2001 | Hottle et al. | |
| 6,231,770 B1 | 5/2001 | Bormann et al. | |
| 6,254,628 B1 | 7/2001 | Wallace et al. | |
| 6,337,026 B1 | 1/2002 | Lee et al. | |
| 6,368,871 B1 | 4/2002 | Christel et al. | |
| 6,387,461 B1 | 5/2002 | Ebner et al. | |
| 6,403,124 B1 | 6/2002 | Dottori | |
| 6,413,713 B1 | 7/2002 | Serebrennikov | |
| 6,439,577 B2 | 8/2002 | Jorgensen et al. | |
| 6,447,987 B1 | 9/2002 | Hess et al. | |
| 6,475,147 B1 | 11/2002 | Yost et al. | |
| 6,482,585 B2 | 11/2002 | Dottori | |
| 6,527,957 B1 | 3/2003 | Deniega et al. | |
| 6,564,207 B1 | 5/2003 | Abdoh | |
| 6,582,496 B1 | 6/2003 | Cheng et al. | |
| 6,610,772 B1 | 8/2003 | Clauberg et al. | |
| 6,688,476 B2 | 2/2004 | Breillatt, Jr. et al. | |
| 6,695,803 B1 | 2/2004 | Robinson et al. | |
| 6,697,667 B1 | 2/2004 | Lee et al. | |
| 6,723,051 B2 | 4/2004 | Davidson et al. | |
| 6,761,695 B2 | 7/2004 | Yost et al. | |
| 6,773,407 B2 | 8/2004 | Yost et al. | |
| 6,817,979 B2 | 11/2004 | Nihtilä | |
| 6,866,783 B2 | 3/2005 | Baurmeister et al. | |
| 6,955,648 B2 | 10/2005 | Mozayeni et al. | |
| 7,097,690 B2 * | 8/2006 | Usher et al. | 95/46 |
| 7,104,958 B2 | 9/2006 | Crutchfield et al. | |
| 7,208,120 B2 | 4/2007 | Bitensky et al. | |
| 7,347,887 B2 | 3/2008 | Bulow et al. | |
| 7,361,277 B2 | 4/2008 | Bormann et al. | |
| 7,431,995 B2 | 10/2008 | Smith et al. | |
| 7,452,601 B2 | 11/2008 | Ebner et al. | |
| 7,721,898 B2 | 5/2010 | Yagi et al. | |
| 7,723,017 B2 | 5/2010 | Bitensky et al. | |
| 7,754,798 B2 | 7/2010 | Ebner et al. | |
| 7,775,376 B2 | 8/2010 | Bonaguidi et al. | |
| 8,071,282 B2 | 12/2011 | Bitensky et al. | |
| 8,535,421 B2 * | 9/2013 | Yoshida et al. | 96/6 |
| 2001/0027156 A1 | 10/2001 | Egozy et al. | |
| 2002/0062078 A1 | 5/2002 | Crutchfield et al. | |
| 2002/0066699 A1 | 6/2002 | Boggs et al. | |
| 2002/0085952 A1 | 7/2002 | Ellingboe et al. | |
| 2002/0086329 A1 | 7/2002 | Shvets et al. | |
| 2002/0099570 A1 | 7/2002 | Knight | |
| 2002/0182241 A1 | 12/2002 | Borenstein et al. | |
| 2003/0003575 A1 | 1/2003 | Vacanti et al. | |
| 2003/0062299 A1 | 4/2003 | Lee et al. | |
| 2003/0124504 A1 | 7/2003 | Bitensky et al. | |
| 2003/0183801 A1 | 10/2003 | Yang et al. | |
| 2003/0189003 A1 | 10/2003 | Kraus et al. | |
| 2003/0233934 A1 * | 12/2003 | Wijmans et al. | 95/46 |
| 2004/0026341 A1 | 2/2004 | Hogberg et al. | |
| 2004/0168982 A1 | 9/2004 | Bitensky et al. | |
| 2005/0038342 A1 | 2/2005 | Mozayeni et al. | |
| 2005/0137517 A1 | 6/2005 | Blickhan et al. | |
| 2005/0139806 A1 | 6/2005 | Havens et al. | |
| 2005/0208462 A1 | 9/2005 | Bitensky et al. | |
| 2005/0210141 A1 | 9/2005 | Oyama et al. | |
| 2005/0233302 A1 * | 10/2005 | Hess et al. | 435/2 |
| 2006/0081524 A1 | 4/2006 | Sengupta et al. | |
| 2006/0118479 A1 | 6/2006 | Shevkoplyas et al. | |
| 2007/0078113 A1 | 4/2007 | Roth et al. | |
| 2007/0240569 A1 | 10/2007 | Ooya | |
| 2008/0160107 A1 | 7/2008 | McCaney et al. | |
| 2008/0276803 A1 * | 11/2008 | Molaison et al. | 96/6 |
| 2009/0017128 A1 | 1/2009 | Monzyk et al. | |
| 2009/0084720 A1 * | 4/2009 | Dannenmaier et al. | 210/188 |
| 2009/0269837 A1 | 10/2009 | Shevkoplyas et al. | |
| 2010/0221697 A1 | 9/2010 | Sehgal | |
| 2010/0313755 A1 | 12/2010 | Koros et al. | |
| 2011/0092875 A1 * | 4/2011 | Beck | 96/6 |
| 2012/0024156 A1 | 2/2012 | Yoshida et al. | |
| 2012/0129148 A1 | 5/2012 | Hess et al. | |
| 2012/0129149 A1 * | 5/2012 | Federspiel et al. | 435/2 |
| 2012/0219633 A1 | 8/2012 | Sowemimo-Coker | |
| 2013/0197420 A1 * | 8/2013 | Fissell et al. | 604/6.16 |
| 2013/0327677 A1 | 12/2013 | McDorman | |

(56) References Cited

U.S. PATENT DOCUMENTS

FOREIGN PATENT DOCUMENTS

| | | |
|---|---|---|
| DE | 10327988 A1 | 7/2004 |
| EP | 0 100 419 A2 | 2/1984 |
| EP | 0 217 759 A1 | 4/1987 |
| EP | 0 299 381 A2 | 1/1989 |
| FR | 2 581 289 A1 | 11/1986 |
| GB | 1 044 649 A2 | 10/1966 |
| JP | 58-194879 | 11/1983 |
| JP | 63-63616 A | 3/1988 |
| JP | 01-104271 A | 4/1989 |
| JP | 5-503075 A | 5/1993 |
| JP | 5-503304 A | 6/1993 |
| JP | 5-305123 A | 11/1993 |
| JP | 06-121920 A | 5/1994 |
| JP | 2700170 B2 | 1/1998 |
| JP | 2000-516963 A | 12/2000 |
| JP | 2002-253936 A | 9/2002 |
| JP | 2004/089495 | 3/2004 |
| JP | 2005-535279 A | 11/2005 |
| JP | 2007-260393 A | 10/2007 |
| JP | 10/501443 | 2/2010 |
| KR | 10-0721054 | 5/2006 |
| SU | 1718766 A1 | 1/1990 |
| WO | WO 81/02239 A1 | 8/1981 |
| WO | WO 86/00809 A1 | 2/1986 |
| WO | WO 89/02274 A1 | 3/1989 |
| WO | WO 91/04659 A1 | 4/1991 |
| WO | WO 92/08348 A1 | 5/1992 |
| WO | WO 95/29662 A2 | 11/1995 |
| WO | WO96/29103 | 9/1996 |
| WO | WO96/29346 | 9/1996 |
| WO | WO 96/29864 A1 | 10/1996 |
| WO | WO97/37628 | 10/1997 |
| WO | WO98/51147 | 11/1998 |
| WO | WO 99/48963 A2 | 9/1999 |
| WO | WO 03/043571 A2 | 5/2003 |
| WO | WO03/086577 | 10/2003 |
| WO | WO 2006-057473 A1 | 6/2006 |
| WO | WO 2009/132839 A1 * | 11/2009 ............. B01D 71/70 |
| WO | WO 2011/014855 A2 | 2/2011 |
| WO | WO 2011/046841 A1 | 4/2011 |
| WO | WO 2012/027582 A1 | 3/2012 |
| WO | WO 2012/061731 A1 | 5/2012 |

OTHER PUBLICATIONS

Anderson et al., "Microfabrication and microfluidics for tissue engineering: state of the art and future opportunities," Lab Chip, 4:98-103 (2004).
Barbee et al., "The Fahraeus Effect," Microvascular Research, 3:6-16 (1971).
Barclay et al., "A Method for Detecting Chaos in Canine Myocardial Microcirculatory Red Cell Flux," Microcirculation, 7(5):335-346 (2000).
Bardy et al., "Technetium-99m Labeling by Means of Stannous Pyrophosphate: Application to Bleomycin and Red Blood Cells," Journal of Nuclear Medicine, 16(5):435-437 (1975).
Barras et al., "Einfluss der Rejuvenation auf die rheologischen Eigenschaften gelagerter Erythrozyten," VASA, 23(4):305-311 (1994).
Beutler et al., "Storage of red cell concentrates in CPD-A2 for 42 and 49 days," The Journal of Laboratory and Clinical Medicine, 102(1):53-62 (1983).
Borenstein et al., "Microfabrication Technology for Vascularized Tissue Engineering," Biomedical Microdevices, 4(3):167-175 (2002).
Brody et al., "Deformation and Flow of Red Blood Cells in a Synthetic Lattice: Evidence for an Active Cytoskeleton," Biophysical Journal, 68:2224-2232 (1995).
Carmen, "The Selection of Plastic Materials for Blood Bags," Transfusion Medicine Reviews, 7(1):1-10 (1993).
Carr et al., "Nonlinear Dynamics of Microvascular Blood Flow," Annals of Biomedical Engineering, 28:641-652 (2000).
Cell Deformability, RheoSCAN (RheoScan-AnD300/RheoScan-D300), obtained on Dec. 11, 2012, from: http://www.rheoscan.com/products/products/products-01.html.
Chilton et al., "Privacy Protection of Health Information: Patient Rights and Pediatrician Responsibilities," Pediatrics, 104(4):973-977 (1999).
Cokelet et al., "Fabrication of in Vitro Microvascular Blood Flow Systems by Photolithography," Microvascular Research, 46:394-400 (1993).
Dale et al., "Human Vaccination with Escherichia coli J5 Mutant Induces Cross-Reactive Bactericidal Antibody against Neisseria gonorrhoeae Lipooligosaccharide," The Journal of Infectious Diseases, 166:316-325 (1992).
De Angelis et al., "Erythrocyte Shape Control in Stored Blood: The Effect of Additive Solutions on Shape Recovery," Haematologica, 73:7-12 (1988).
Deible et al., "Molecular barriers to biomaterial thrombosis by modification of surface proteins with polyethylene glycol," Biomaterials, 19:1885-1893 (1998).
De Venuto et al., "Rejuvenation of Human Red Blood Cells During Liquid Storage," Transfusion, 14(4):338-344 (1974).
Dumaswala et al., "Studies in Red Blood Cell Preservation: 9. The Role of Glutamine in Red Cell Preservation," Vox Sang, 67:255-259 (1994).
Dumaswala et al., "Glutamine- and Phosphate-Containing Hypotonic Storage Media Better Maintain Erythrocyte Membrane Physical Properties," Blood, 88(2):697-704 (1996).
Dumaswala et al., "Improved Red Blood Cell Preservation Correlates With Decreased Loss of Bands 3, 4.1, Acetylcholinestrase, and Lipids in Microvesicles," Blood, 87(4):1612-1616 (1996).
Dumont et al., "Anaerobic storage of red blood cells in a novel additive solution improves in vivo recovery," Transfusion, 49(3):458-464 (2009).
Effenhauser et al., "Integrated Capillary Electrophoresis on Flexible Silicone Microdevices: Analysis of DNA Restriction Fragments and Detection of Single DNA Molecules on Microchips," Anal. Chem., 69:3451-3457 (1997).
European Search Report completed on Feb. 11, 2005, in European Patent Application No. 02 78 2307.9.
Fahraeus et al., "The Viscosity of the Blood in Narrow Capillary Tubes," Am. J. Physiol., 96(3):562-568 (1931).
Fang et al., "Inhibition of Lipopolysaccharide-Associated Endotoxin Activities In Vitro and In Vivo by the Human Anti-Lipid A Monoclonal Antibody SdJ5-1.17.15," Infection and Immunity, 61(9):3873-3878 (1993).
Frame et al., "A System for Culture of Endothelial Cells in 20-50-µm Branching Tubes," Microcirculation, 2(4):377-385 (1995).
Fung et al., "High-Resolution Data on the Geometry of Red Blood Cells", Biorheology, 18:369-385 (1981).
Gañán-Calvo et al., "Current and Droplet Size in the Electrospraying of Liquids. Scaling Laws," J Aerosol Sci., 28(2):249-275 (1997).
Green et al., "10. Liposomal Vaccines," Immunobiology of Proteins and Peptides VII, Plenum Press, New York, pp. 83-92 (1995).
Greenwalt et al., "Studies in Red Blood Cell Preservation. 7. In vivo and in Vitro Studies with a Modified Phosphate-Ammonium Additive Solution," Vox Sang, 65:87-94 (1993).
Greenwalt et al., "Studies in Red Blood Cell Preservation. 8. Liquid Storage of Red Cells in Glycerol-Containing Additive Solution," Vox. Sang, 67:139-143 (1994).
Greenwalt et al., "Studies in red blood cell preservation. 10. $^{51}$Cr Recovery of Red Cells after Liquid Storage in a Glycerol-Containing Additive Solution," Vox Sang, 70:6-10 (1996).
Greenwalt et al., "The effect of hypotonicity, glutamine, and glycine on red cell preservation," Transfusion, 37:269-276 (1997).
Griffith, "Temporal chaos in the microcirculation," Cardiovascular Research, 31:342-358 (1996).
Hamasaki et al., "Acid-citrate-dextrose-phosphoenolpyruvate medium as a rejuvenant for blood storage," Transfusion, 23(1):1-7 (1983).

(56) References Cited

OTHER PUBLICATIONS

Hess, "Extended Liquid Storage of Red Blood Cells," Blood Donors and the Supply of Blood and Blood Products, National Academy Press, Washington, D.C., pp. 99-102 (1996).
Hess et al., "Successful storage of RBCs for 9 weeks in a new additive solution," *Transfusion*, 40:1007-1011 (2000).
Hess, "Storage of red blood cells under anaerobic conditions," *Vox Sanguinis*, 93:183 (2007).
Hodgson et al., "Prophylactic use of human endotoxin-core hyperimmune gammaglobulin to prevent endotoxaemia in colostrum-deprived, gnotobiotic lambs challenged orally with *Escherichia coli*," *FEMS Immunology and Medical Microbiology*, 11:171-180 (1995).
Högman et al., "Cell Shape and Total Adenylate Concentration as Important Factors for Posttransfusion Survival of Erythrocytes," *Biomed. Biochim. Acta*, 42:S327-S331 (1983).
Högman et al.,"Effects of Oxygen on Red Cells during Liquid Storage at +4° C.," *Vox Sang.*, 51:27-34 (1986).
Högman et al., "Effects of Oxygen and Mixing on red cells stored in plastic bags at +4° C.," *Biomed. Biochim. Acta.*, 46:S290-S294 (1987).
Högman et al., "Shall Red Cell Units Stand Upright, Lie Flat or be Mixed During Storage? In Vitro Studies of Red Cells Collected in 0.5 CPD and Stored in RAS2 (Erythrosol®)," *Transfus. Sci.*, 16(2):193-199 (1995).
Huang et al., "Continuous Particle Separation Through Deterministic Lateral Displacement," *Science*, 304:987-990 (2004).
International Preliminary Report on Patentability completed on May 21, 2012, in International Patent Application No. PCT/US2010/52376.
International Preliminary Report on Patentability completed on Oct. 18, 2011, in International Patent Application No. PCT/US2010/031055.
International Search Report completed on Jul. 8, 1996, in International Patent Application No. PCT/US96/09005.
International Search Report completed on Nov. 10, 2003, in International Patent Application No. PCT/US02/36735.
International Search Report completed on May 20, 2010, in International Patent Application No. PCT/US2010/31055.
International Search Report completed on Nov. 22, 2010, in International Patent Application No. PCT/US2010/052376.
International Search Report completed on Feb. 8, 2011, in International Patent Application No. PCT/US10/52084.
International Search Report completed on Dec. 21, 2011, in International Patent Application No. PCT/US11/49168.
International Search Report completed on Feb. 12, 2012, in International Patent Application No. PCT/US11/59372.
International Search Report completed on Jun. 18, 2012, in International Patent Application No. PCT/US12/30930.
International Search Report completed on Sep. 24, 2012, in International Patent Application No. PCT/US12/50380.
Jain, et al., "Determinants of Leukocyte Margination in Rectangular Microchannels," *PLoS One*, 4(9):1-8 (2009).
Jayasinghe et al., "Controlled deposition of nanoparticle clusters by electrohydrodynamic atomization," *Nanotechnology*, 15:1519-1523 (2004).
Jiang et al., "Microfluidic synthesis of monodisperse PDMS microbeads as discrete oxygen sensors," *Soft Matter*, 8:923-926 (2011).
Jo et al., "Surface modification using silanated poly(ethylene glycol)s," *Biomaterials*, 21:605-616 (2000).
Johnson et al., "Regulation of blood flow in single capillaries," *American Journal of Physiology*, 212:1405-1415 (1967).
Kaihara et al., "Silicon Micomachining to Tissue Engineer Branched Vascular Channels for Liver Fabrication," *Tissue Engineering*, 6(2):105-117 (2000).
Kiani et al., "Fluctuations in microvascular blood flow parameters caused by hemodynamic mechanisms," *American Journal of Physiology*, 266(5):H1822-H1828 (1994).

Kikuchi et al., "Modified Cell-Flow Microchannels in a Single-Crystal Silicon Substrate and Flow Behavior of Blood Cells," *Microvascular Research*, 47:126-139 (1994).
Koch et al., "Peripheral blood leukocyte NO production and oxidative stress in multiple sclerosis," *Multiple Sclerosis*, 14:159-165 (2008).
Koch et al., "Duration of Red-Cell Storage and Complications After Cardiac Surgery," *The New England Journal of Medicine*, 358:1229-1239 (2008).
Krogh, "Studies on the physiology of capillaries. II. The reactions to local stimuli of the blood-vessels in the skin and web of the frog," *The Journal of Physiology*, 55:412-422 (1921).
Kuraoka, et al., "Ship-in-a-bottle synthesis of a cobalt phthalocyanine/porous glass composite membrane for oxygen separation," *Journal of Membrane Science*, 286(1-2):12-14 (2006).
Lugowski et al., "Anti-endotoxin antibodies directed against *Escherichia coli* R-1 oligosaccharide core-tetanus toxoid conjugate bind to smooth, live bacteria and smooth lipopolysaccharides and attenuate their tumor necrosis factor stimulating activity," *FEMS Immunology and Medical Microbiology*, 16:31-38 (1996).
Mazor et al., "Prolonged Storage of Red Cells: The Effect of pH, Adenine Phosphate," *Vox Sanguinis*, 66:264-269 (1994).
McDonald et al., "Poly(dimethylsiloxane) as a Material for Fabricating Microfluidic Devices," *Accounts of Chemical Research*, 35(7):491-499 (2002).
Meryman et al., "Prolonged storage of red cells at 4° C.," *Transfusion*, 26(6):500-505 (1986).
Meryman et al., "Extending the storage of red cells at 4° C.," *Transfus. Sci.*, 15(2):105-115 (1994).
Moll et al., "Dean vortices applied to membrane process. Part II: Numerical approach," *Journal of Membrane Science*, 288:321-335 (2007).
Moroff et al., "Proposed standardization of methods for determining the 24-hour survival of stored red cells," *Transfusion*, 24:109-114 (1984).
Murphy et al., "Increased Mortality, Postoperative Morbidity, and Cost After Red Blood Cell Transfusion in Patients Having Cardiac Surgery," *Circulation*, 116:2544-2552 (2007).
Ng et al., "Components for integrated poly(dimethylsiloxane) microfluidic systems," *Electrophoresis*, 23:3461-3473 (2002).
Ohkuma et al., "The preservative-exchange method using a sextuple-bag system for a 10-week storage period of red blood cells," *Transfusion Medicine*, 1:257-262 (1991).
Poxton, "Antibodies to lipopolysaccharide," *Journal of Immunological Methods*, 186:1-15 (1995).
Pries et al., "Biophysical aspects of blood flow in the microvasculature," *Cardiovascular Research*, 32:654-667 (1996).
Sambuceti et al., "Why should we study the coronary microcirculation?," *Am J Physiol Heart Circ Physiol*, 279:H2581-H2584 (2000).
Shevkoplyas et al., "Direct measurement of the impact of impaired erythrocyte deformability on microvascular network perfusion in a microfluidic device," *Lab Chip*, 6:914-920 (2006).
Shimizu et al., "Multicenter Clinical Evaluation of Red Cell Concentrates Stored up to 6 Weeks in MAP, a new additive solution," *Japanese Journal of Clinical Hematology*, 33(2):148-156 (1992).
Skalak et al., "Deformation of Red Blood Cell in Capillaries," *Science*, 164(3880):717-719 (1969).
Sohmer et al., "Phosphoenolypyruvate (PEP) Effects on Fresh and Stored Red Blood Cells," *Proceedings of the Society for Experimental Biology and Medicine*, 171:24-33 (1982).
Sutton et al., "A Novel Instrument for Studying the Flow Behaviour of Erythrocytes through Microchannels Simulating Human Blood Capillaries," *Microvascular Research*, 53:272-281 (1997).
Szymanski et al., "Effect of rejuvenation and frozen storage on 42-day-old AS-1 RBCs," *Transfusion*, 41:550-555 (2001).
The International Committee for Standardization in Hematology, "Recommended Methods for Radioisotope Red Cell Survival Studies," *Blood*, 38(3):378-386 (1971).
Tinmouth et al., "The Clinical Consequences of the Red Cell Storage Lesion," *Transfusion Medicine Reviews*, 15(2):91-107 (2001).
Tracey et al., "A Silicon Micromachined Device for Use in Blood Cell Deformability Studies," *IEEE Transactions on Biomedical Engineering*, 42(8):751-761 (1995).

(56) References Cited

OTHER PUBLICATIONS

Tsukada et al., "Direct Measurement of Erythrocyte Deformability in Diabetes Mellitus with a Transparent Microchannel Capillary Model and High-Speed Video Camera System," *Microvascular Research*, 61:231-239 (2001).

Valeri et al., "The survival, function, and hemolysis of human RBCs stored at 4° C. in additive solution (AS-1, AS-3, or AS-5) for 42 days and then biochemically modified, frozen, thawed, washed, and stored at 4° C. in sodium chloride and glucose solution for 24 hours," *Transfusion*, 40:1341-1345 (2000).

Wang et al., "Fabrication of PLGA microvessel scaffolds with circular microchannels using soft lithography," *Journal of Micromechanics and Microengineering*, 17(10):2000-2005 (2007).

Weinberg et al., "Transfusions in the Less Severely Injured: Does Age of Transfused Blood Affect Outcomes?," *The Journal of Trauma*, 65(4):794-798 (2008).

Wilding et al., "Manipulation and Flow of Biological Fuids in Straight Channels Micromachined in Silicon," *Clinical Chemistry*, 40(1):43-47 (1994).

Wood et al., "The Viability of Human Blood Stored in Phosphate Adenine Media," *Transfusion*, 7(6):401-408 (1967).

Wu et al., "Polymer microchips bonded by $O_2$-plasma activation," *Electrophoresis*, 23:782-790 (2002).

Yoshida et al., "Extended storage of red blood cells under anaerobic conditions," *Vox Sanguinis*, 92:22-31 (2007).

Yoshida et al., "Storage of red blood cells under anaerobic conditions: reply," *Vox Sanguinis*, 93:184 (2007).

Yoshida et al., "The effects of additive solution pH and metabolic rejuvenation on anaerobic storage of red cells," *Transfusion*, 48:2096-2105 (2008).

Yoshida et al., "Anaerobic storage of red blood cells," *Blood Transfus*, 8:220-236 (2010).

Zhang et al., "Modification of Si(100) surface by the grafting of poly(ethylene glycol) for reduction in protein adsorption and platelet adhesion," *J Biomed Mater Res*, 56:324-332 (2001).

Zimrin et al., "Current issues relating to the transfusion of stored red blood cells," *Vox Sanguinis*, 96:93-103 (2009).

Burns et al., "Artificial microvascular network: a new tool for measuring rheologic properties of stored red blood cells," *Transfusion*, 52(5):1010-1023 (2012).

Durapore® Membrane Filters—Filter Discs and Membranes, retrieved on Aug. 26, 2014, from: www.emdmillipore.com/US/en/product/Durapore.

Gifford et al., "Parallel Microchannel-Based Measurements of Individual Erythrocyte Areas and Volumes," *Biophysical Journal*, 84:623-633 (2003).

Gifford el al., "A detailed study of time-dependent changes in human red blood cells: from reticulocyte maturation to erythrocyte senescence," *British Journal of Haematology*, 135:395-404 (2006).

Holme et al., "Current Issues Related to the Quality of Stored RBC's," *Transfusion and Apheresis Science*, Elsevier Science, 33(1):55-61 (2005).

Prefiltration before membrane filtration, hydrophobic, 25 µm 142 mm, retrieved on Aug. 26, 2014, from: www.emdmillipore.com/US/en/product/Prefiltration-before-membrane-filtration.

International Search Report and Written Opinion issued in International Patent Application PCT/US2014/019537 dated Jul. 10, 2014.

Extended European Search Report, dated Aug. 8, 2014 for European Patent Application No. 10823965.8.

Extended European Search Report, dated Oct. 23, 2014 for European Patent Application No. 11838889.1.

Extended European Search Report dated Oct. 24, 2014 in European Patent Application No. 12807324.4.

Supplementary European Search Report dated Jan. 20, 2015 in European Patent Application No. 12822378.2.

* cited by examiner

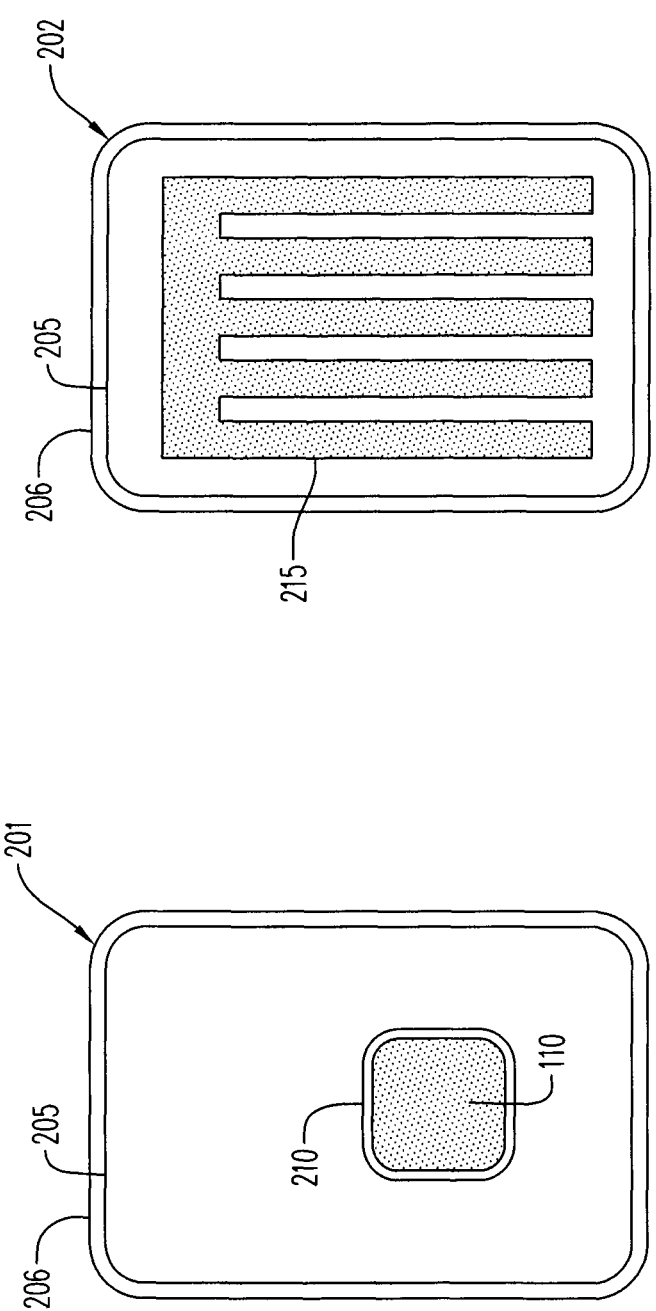

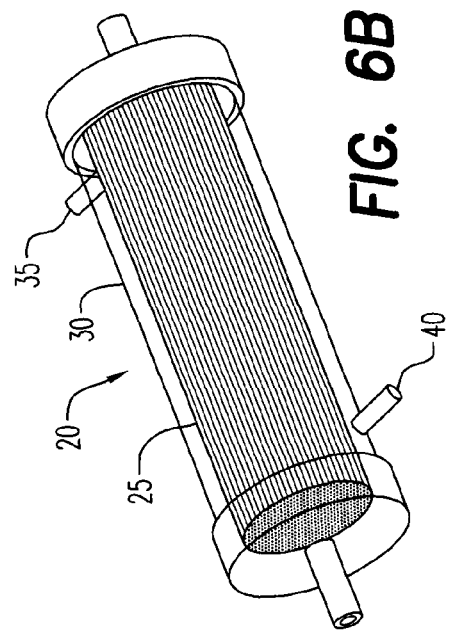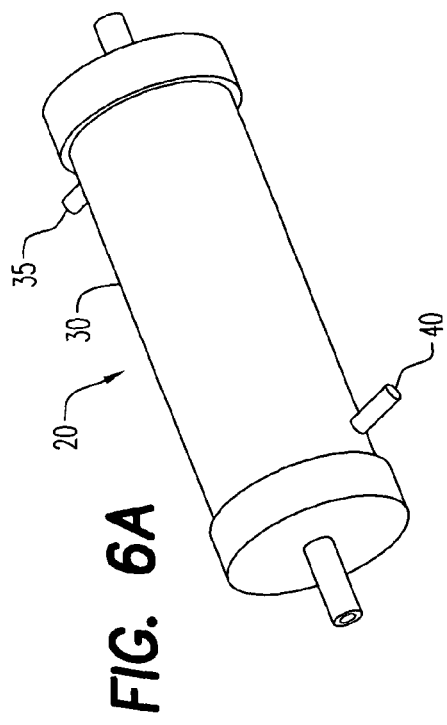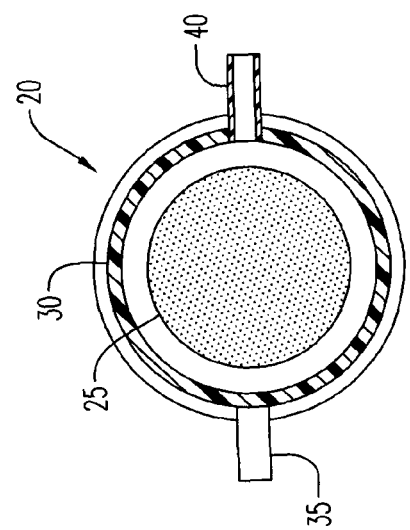

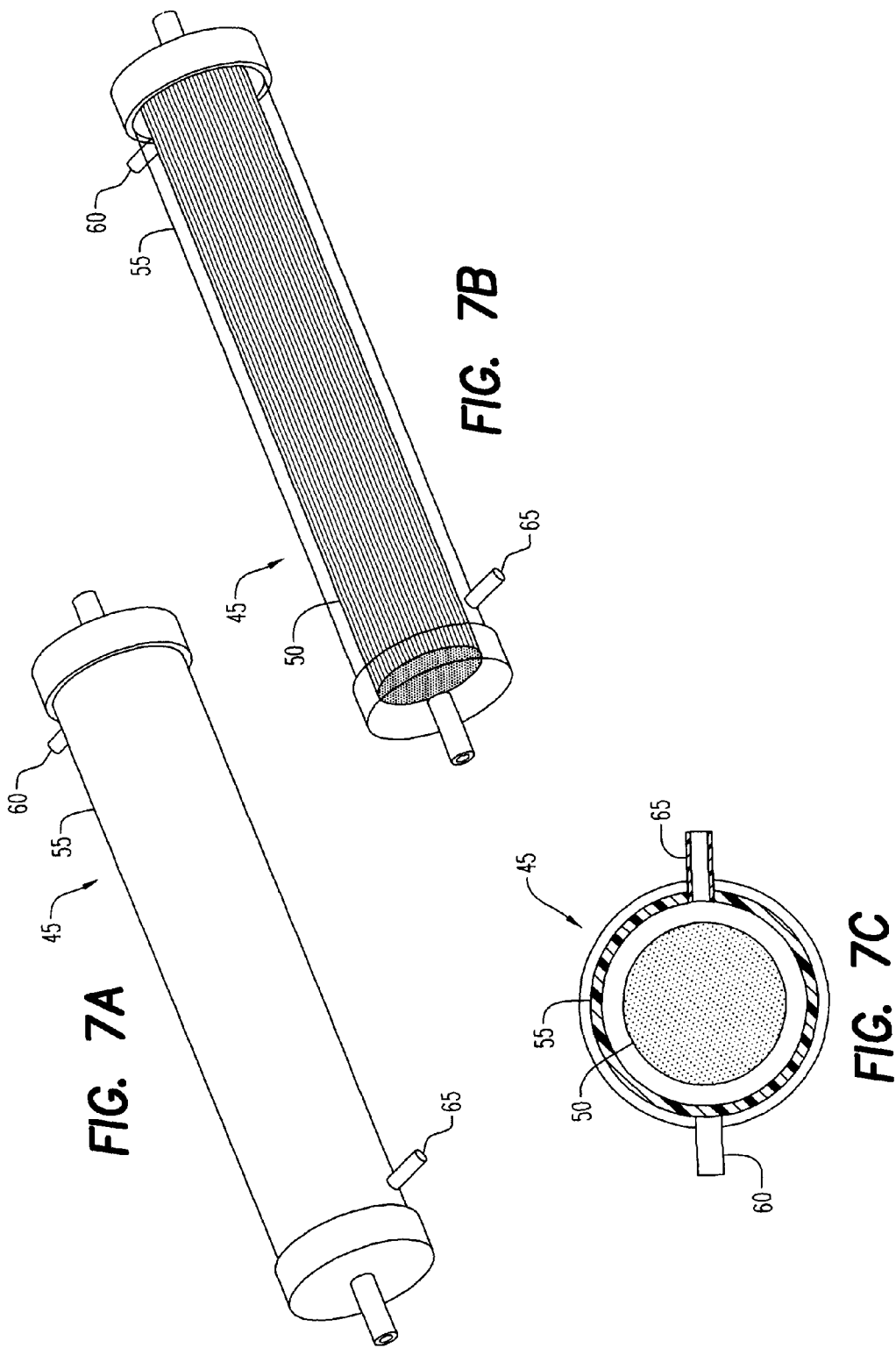

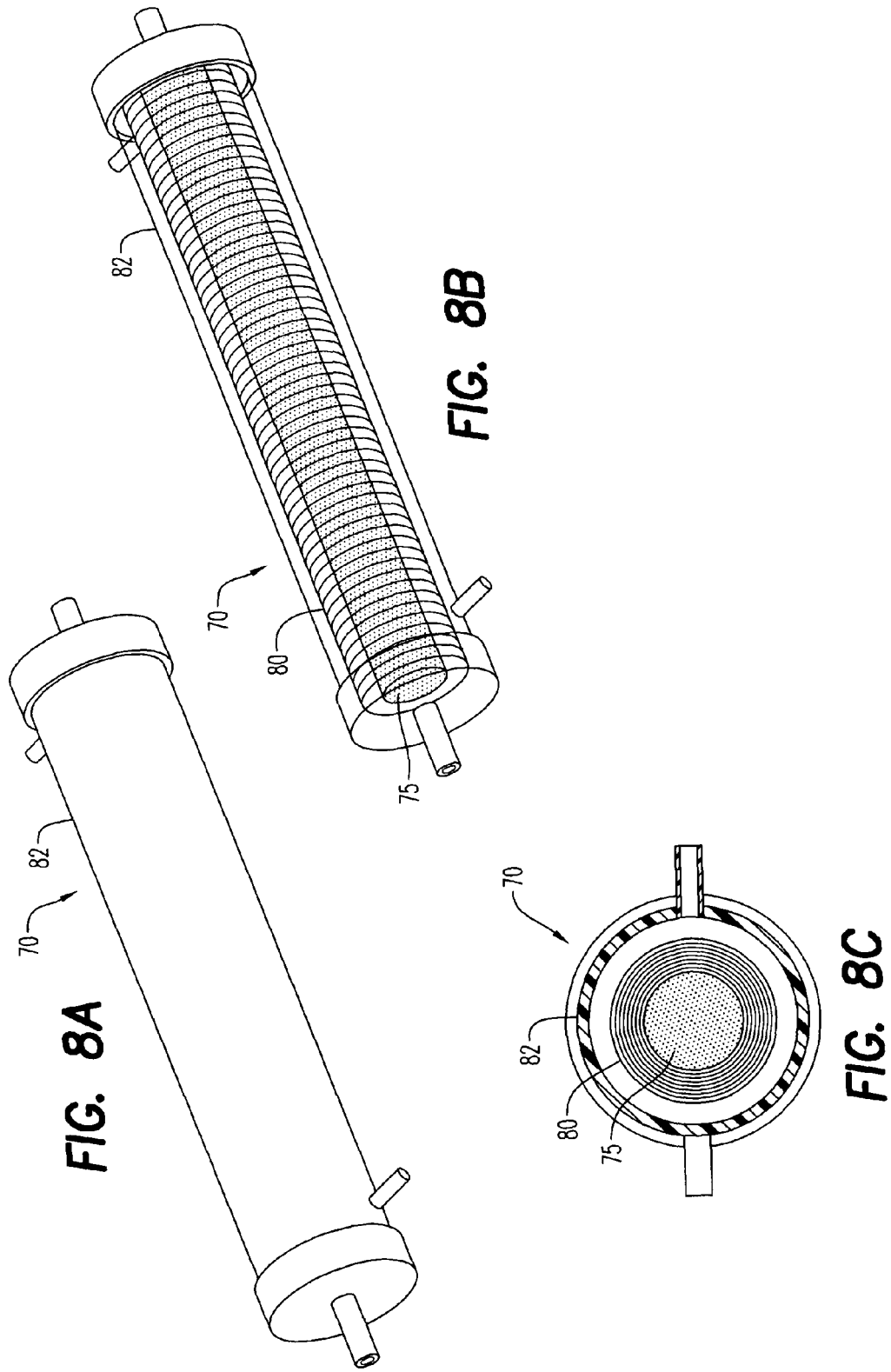

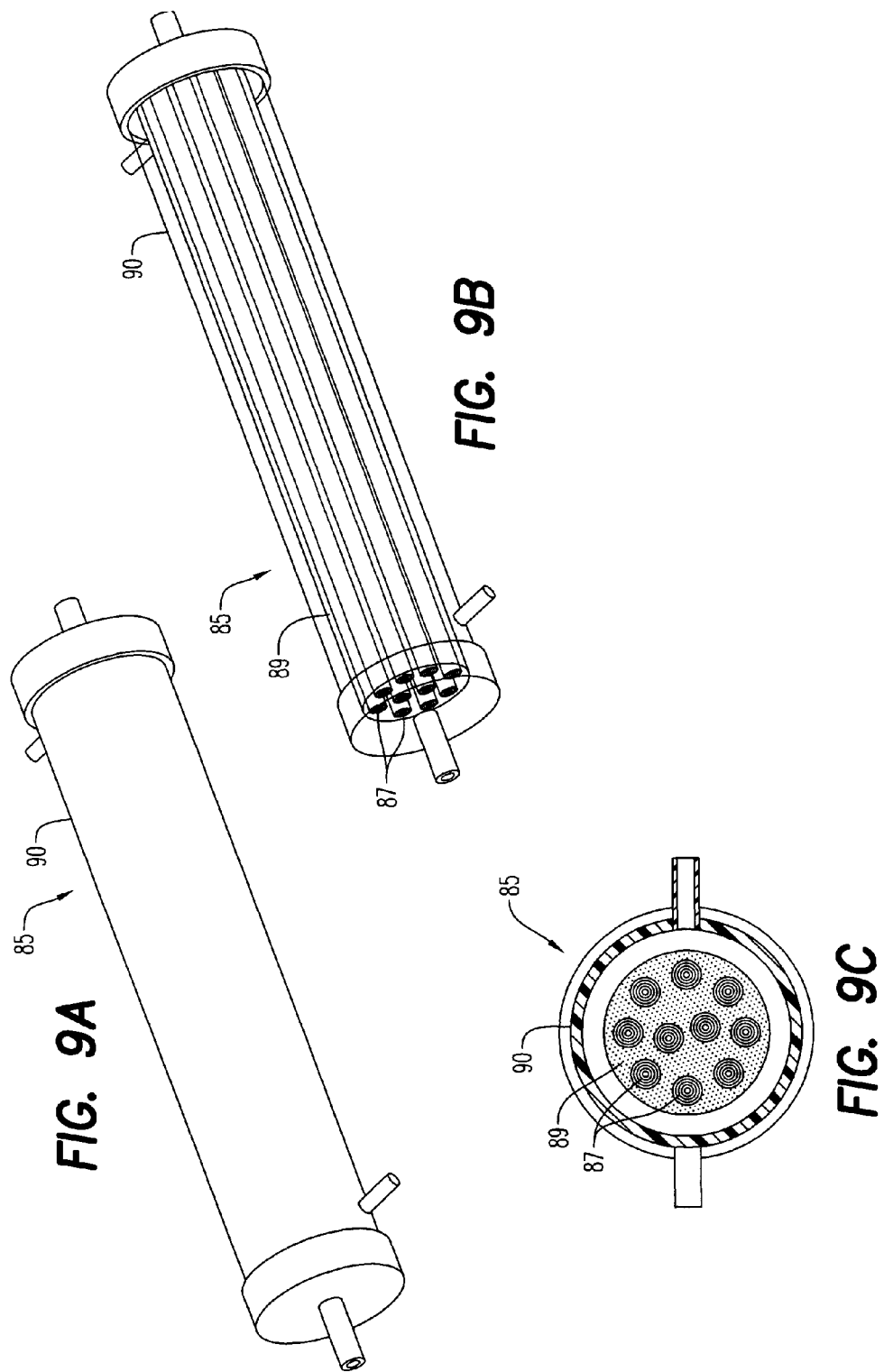

BLOOD STORAGE BAG SYSTEM AND DEPLETION DEVICES WITH OXYGEN AND CARBON DIOXIDE DEPLETION CAPABILITIES

CROSS-REFERENCE TO RELATED APPLICATIONS

This application is a continuation application of U.S. patent application Ser. No. 12/901,350, filed Oct. 8, 2010, now U.S. Pat. No. 8,535,421, issued Sep. 17, 2013, which claims the benefit under 35 U.S.C. §119(e) of U.S. Provisional Application No. 61/331,693, filed May 5, 2010 and U.S. Provisional Application No. 61/250,661, filed Oct. 12, 2009, all of which are hereby incorporated by reference in their entireties.

BACKGROUND

1. Field

The present disclosure relates to a storage blood system having an oxygen/carbon dioxide depletion device and a blood storage bag for the long-term storage of blood. More particularly, the present disclosure relates to a blood storage system that is capable of removing oxygen and carbon dioxide from the red blood prior to storage and during storage, as well as maintaining oxygen and/or carbon dioxide depleted states during storage, thereby prolonging the storage life and minimizing deterioration of the deoxygenated red blood.

2. Background of the Art

Adequate blood supply and the storage thereof is a problem facing every major hospital and health organization around the world. Often, the amount of blood supply in storage is considerably smaller than the need therefor. This is especially true during crisis periods such as natural catastrophes, war and the like, when the blood supply is often perilously close to running out. It is at critical times such as these that the cry for more donations of fresh blood is often heard. However, unfortunately, even when there is no crisis period, the blood supply and that kept in storage must be constantly monitored and replenished, because stored blood does not maintain its viability for long.

Stored blood undergoes steady deterioration which is, in part, caused by hemoglobin oxidation and degradation and adenosine triphosphate (ATP) and 2-3,biphosphoglycerate (DPG) depletion. Oxygen causes hemoglobin (Hb) carried by the red blood cells (RBCs) to convert to met-Hb, the breakdown of which produces toxic products such as hemichrome, hemin and free $Fe^{3+}$. Together with the oxygen, these products catalyze the formation of hydroxyl radicals (OH.cndot.), and both the OH.cndot. and the met-Hb breakdown products damage the red blood cell lipid membrane, the membrane skeleton, and the cell contents. As such, stored blood is considered unusable after 6 weeks, as determined by the relative inability of the red blood cells to survive in the circulation of the transfusion recipient. The depletion of DPG prevents adequate transport of oxygen to tissue thereby lowering the efficacy of transfusion immediately after administration (levels of DPG recover once in recipient after 8-48 hrs). In addition, these deleterious effects also result in reduced overall efficacy and increased side effects of transfusion therapy with stored blood before expiration date, but possibly older than two weeks are used. Reduction in carbon dioxide content in stored blood has the beneficial effect of elevating DPG levels in red blood cells.

There is, therefore, a need to be able to deplete oxygen and carbon dioxide levels in red blood cells prior to storage on a long-term basis without the stored blood undergoing the harmful effects caused by the oxygen and hemoglobin interaction. Furthermore, there is a need to store oxygen and carbon dioxide depleted red blood cells in bags containing or bag surrounded by a barrier film with oxygen and carbon dioxide depletion materials. Furthermore, there is a need to optimize ATP and DPG levels in stored red blood cells by varying the depletion or scavenging constituents prior to and/or during storage depending upon the needs of the recipient upon transfusion. Furthermore, the blood storage devices and methods must be simple, inexpensive and capable of long-term storage of the blood supply.

SUMMARY

A disposable device for blood storage that is able to deplete of oxygen and anaerobically store of red blood cells for transfusion.

The present disclosure also provides for a device and method of removing carbon dioxide ($CO_2$) in addition to oxygen ($O_2$) prior to or at the onset of anaerobic storage.

The present disclosure further provides for mixing $O_2$ and $CO_2$ scavenging materials that are placed in a depletion device to obtain optimal ATP and DPG levels.

The present disclosure also provides for a depletion device that has the ability to scavenge $CO_2$ prior to or at the onset of anaerobic storage.

The present disclosure further provides for the anaerobic storage bag that is capable of storing red blood cells anaerobically and in a $CO_2$ depleted state.

The present disclosure provides for mixing of $O_2$ and $CO_2$ scavenging materials to be placed in a sachet or incorporated into the storage bag materials of construction within an anaerobic storage bag.

Accordingly, the present disclosure provides for a disposable device for blood storage that is able to deplete oxygen and carbon dioxide as well as anaerobically store red blood cells for transfusion.

The present disclosure also provides for a system the anaerobic storage of RBCs with pre-storage oxygen and carbon dioxide depletion and continued maintenance of the anaerobic and carbon dioxide depleted state during storage.

The present disclosure further provides for the anaerobic storage of standard storage bags by storing them in a controlled-atmosphere container or chamber such as in an inert gas within a refrigerator.

The present disclosure provides for a blood collection system that incorporates an oxygen/carbon dioxide depletion device having an oxygen and carbon dioxide sorbent in combination with a filter or membrane to strip oxygen and carbon dioxide from the blood during transport to the storage bag.

The present disclosure provides for a blood collection system the incorporates an oxygen/carbon dioxide depletion device that contains a gas permeable film or membrane providing sufficient surface area to facilitate diffusion of oxygen and carbon dioxide from the blood into the interior of the device.

The present disclosure provides for a blood collection system that incorporates an oxygen/carbon dioxide depletion device having an oxygen and carbon dioxide sorbent enclosed in gas permeable membrane with a filter or membrane to strip oxygen and carbon dioxide from the blood during transport to the storage bag.

The present disclosure also provides for a laminated storage bag for storing red blood cells (RBCs). The storage bag may be a laminated bag having an oxygen and carbon dioxide sorbent or a secondary bag containing an oxygen and carbon dioxide sorbent.

The present disclosure further provides for a system to deplete the oxygen and carbon dioxide from collected red blood cells that includes an additive solution, an oxygen and carbon dioxide depletion device, and a blood storage bag that maintains the red blood cells in an oxygen and carbon dioxide depleted state.

The present disclosure provides for a system and methodology that permits reduction in carbon dioxide levels prior to storage and an increase in DPG levels. By keeping carbon dioxide levels low, and, thus, DPG levels high, the affinity of oxygen to hemoglobin to bind oxygen is reduced. By having a lower affinity to hemoglobin, greater transmission of oxygen to tissue is permitted.

The present disclosure provides for a method of optimizing ATP and DPG in red blood cells for storage by obtaining a sample of red blood cells from a donor; depleting oxygen and carbon dioxide levels in the sample to produce an oxygen and carbon dioxide depleted sample; storing the oxygen and carbon dioxide depleted sample in a container that maintains oxygen and carbon dioxide depleted state of the sample. The range of depletion is variable.

The present disclosure also provides for optimizing stored blood by treating the stored blood subject to a depletion device having the appropriate levels of oxygen and carbon dioxide gas passed therethrough or with the appropriate blend of oxygen and carbon dioxide depleting scavengers to obtain a desired level of constituents. The blood is also stored under oxygen and or carbon dioxide depleted conditions. Immediately prior to transfusion, re-oxygenating of the stored blood as needed based on the needs of the recipient prior to transfusion.

The present disclosure also provides another embodiment of a blood storage device. The device is a sealed receptacle adapted to retain and store red blood cells. The receptacle has walls formed from a laminate. The laminate has (a) an outer layer of a material substantially impermeable to oxygen and carbon dioxide, (b) an inner layer of a material compatible with red blood cells, and (c) an interstitial layer between the outer layer and the inner layer. The interstitial layer is of a material having admixed therein an amount of either or both of an oxygen scavenger and a carbon dioxide scavenger. Alternately, the interstitial layer can be deleted and the scavenger(s) admixed into the inner and/or outer layer.

The present disclosure also provides another embodiment of a blood storage system. The system has a collection bag for red blood cells; a unitary device for depleting oxygen and carbon dioxide and reducing leukocytes and/or platelets from red blood cells; a storage bag for red blood cells; and tubing connecting the collection bag to the unitary device and the unitary device to the storage bag.

The present disclosure and its features and advantages will become more apparent from the following detailed description with reference to the accompanying drawings.

BRIEF DESCRIPTION OF THE DRAWINGS

FIG. 4a illustrates a pre-storage oxygen/carbon dioxide depletion bag having a blood storage bag with a large sorbent sachet enclosed in gas-permeable, red blood cell compatible polymers in contact with the RBCs.

FIG. 4b illustrates a third embodiment of a blood storage bag having a storage bag a laminated oxygen film barrier with a large sorbent in contact with the RBCs.

FIGS. 6a through 6c illustrate an embodiment of a depletion device that depletes oxygen and carbon dioxide from red blood cells prior to storage by a flushing inert gas or inert gas/$CO_2$ mixture of defined composition around a hollow fiber inside the assembly.

FIGS. 7a through 7c illustrate another embodiment of a depletion device that depletes oxygen and carbon dioxide from red blood cell prior to storage.

FIGS. 8a through 8c illustrate another embodiment of a depletion device that depletes oxygen and carbon dioxide from red blood cells prior to storage wherein oxygen and/or $CO_2$ is scavenged by scavenger materials in the core of the cylinder, surrounded by hollow fibers.

FIGS. 9a through 9c illustrate another embodiment of a depletion device that depletes oxygen and carbon dioxide from red blood cells prior to storage wherein oxygen and/or $CO_2$ is scavenged by scavenger materials surrounding cylinders of hollow fibers enveloped in gas permeable, low water vapor transmission material.

DETAILED DESCRIPTION OF THE PREFERRED EMBODIMENT

Figure 1:
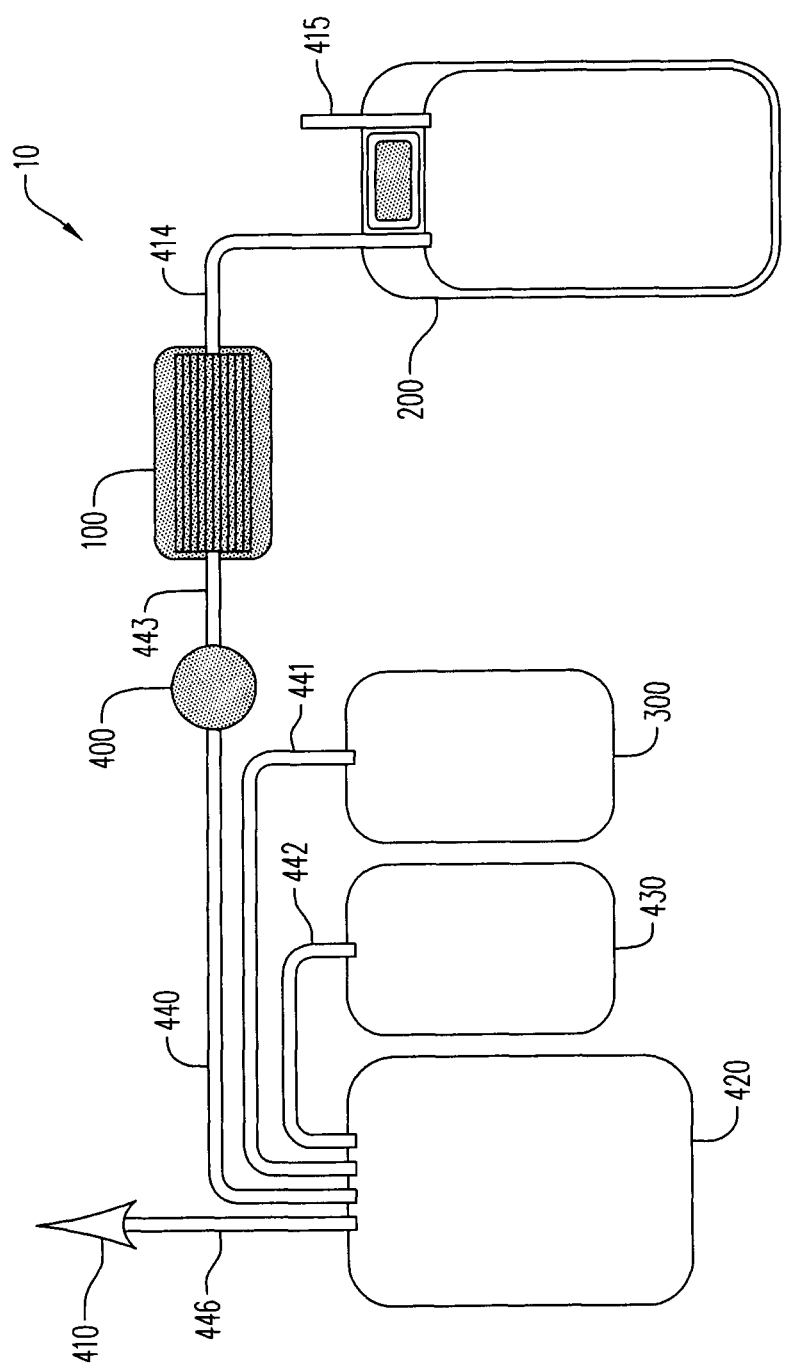
FIG. 1 illustrates the components of a disposable blood anaerobic storage system of the present disclosure.

Referring to the drawings and in particular to FIG. 1, a disposable blood anaerobic storage system is shown and referenced using reference numeral 10. The blood storage system includes an oxygen/carbon dioxide depletion device 100 (OCDD 100), an anaerobic blood storage bag 200 and an additive solution bag 300 stored. OCDD 100 removes oxygen and carbon dioxide from red blood cells traveling through it. The system also contains a leuko reduction filter 400. Components conventionally associated with the process of blood collection are a phlebotomy needle 410, a blood collection bag 420 containing an anti-coagulant and a bag 430 containing plasma. Tubing can connect the various components of the blood storage system 10 in various configurations (one embodiment shown). Tube 440 connects collection bag 420 with leuko reduction filter 400. Tube 441 connects solution bag 300 with collection bag 420. Tube 442 connects plasma bag 430 with collection bag 420. Tube 443 connects leuko reduction filter 400 with OCDD 100. Tube 444 connects OCDD 100 with blood storage bag 200. Blood storage system 10 is preferably a single-use, disposable, low cost system.

Oxygen/carbon dioxide depletion device 100 removes the oxygen from collected RBCs prior to the RBCs being stored in blood storage bag 200. The oxygen content in RBCs must be depleted from oxy-hemoglobin because more than 99% of such oxygen is hemoglobin-bound in venous blood. Preferably, the degree of oxygen saturation is to be reduced to less than 4% within 48 hours of blood collection. The oxygen depletion is preferably accomplished at room temperature. The affinity of oxygen to hemoglobin is highly dependent on the temperature, with a p50 of 26 mmHg at 37° C. dropping to ~4 mmHg at 4° C. Furthermore, this increase in $O_2$ affinity (Ka) is mainly due to reduction in $O_2$ release rate (k-off), resulting in an impractically low rate of oxygen removal once RBC is cooled to 4° C. Thus, it places a constraint on oxygen stripping such that it may be preferable to accomplish it before RBC are cooled to storage temperatures of 1° C. to 6° C.

As an alternative or in addition to oxygen depletion, carbon dioxide depletion has the beneficial effect of elevating DPG levels in red blood cells. Carbon dioxide exists inside RBCs and in plasma in equilibrium with $HCO_3^-$ ion (carbonic acid). Carbon dioxide is mainly dissolved in RBC/plasma mixture as carbonic acid and rapid equilibrium between $CO_2$ and carbonic acid is maintained by carbonic anhydrase inside RBC. Carbon dioxide is freely permeable through RBC membrane, while $HCO_3^-$ inside RBC and plasma is rapidly equilibrated by anion exchanger (band 3) protein. When $CO_2$ is removed from RBC suspension, it results in the known alkalization of RBC interior and suspending medium. This results from removal of $HCO_3^-$ inside and outside RBC; cytosolic $HCO_3^-$ is converted to $CO_2$ by carbonic anhydrase and removed, while plasma $HCO_3^-$ is removed via anion exchange inside RBC. Higher pH inside RBC is known to enhance the rate of glycolysis and thereby increasing ATP and DPG levels. ATP levels are higher in $Ar/CO_2$ ($p<0.0001$). DPG was maintained beyond 2 weeks in the Argon purged arm only ($p<0.0001$). Enhanced glycolysis rate is also predicted by dis-inhibition of key glycolytic enzymes via metabolic modulation and sequesterization of cytosolic-free DPG upon deoxygenation of hemoglobin as a result of anaerobic condition. DPG was lost at the same rate in both control and $Ar/CO_2$ arms ($p=0.6$) despite thorough deoxygenation of hemoglobin, while very high levels of ATP were achieved with OFAS3 additive (FIGS. 11a-d).

Figure 12:
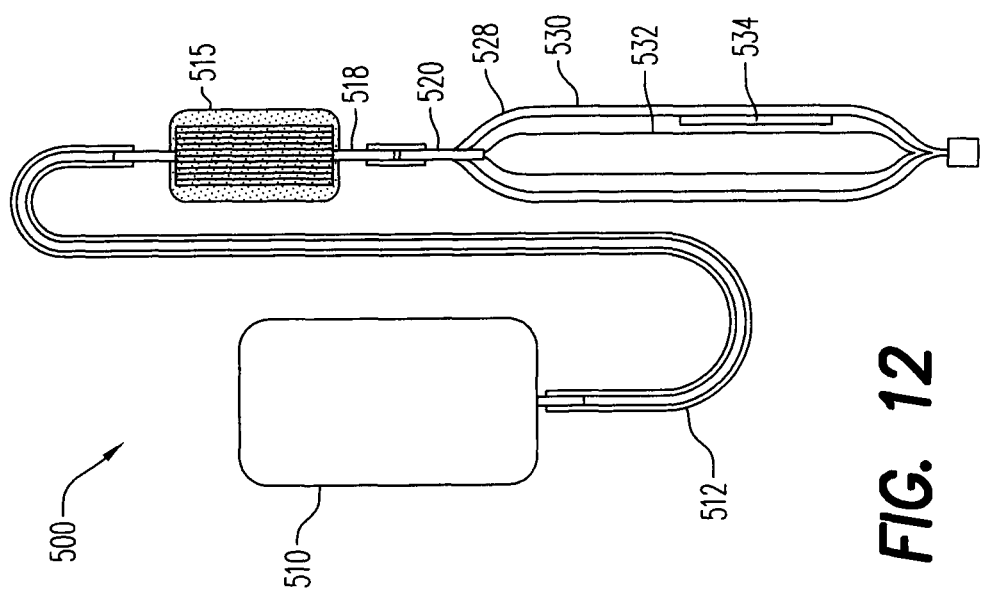
FIG. 12 illustrates the components of another embodiment of a disposable blood anaerobic storage system of the present disclosure.

Referring to the drawings and in particular to FIG. 12, another embodiment of a disposable blood anaerobic storage system is shown and referenced using reference numeral 500. The blood storage system includes a blood collection bag 510, an oxygen/carbon dioxide depletion device 535 (OCDD 535) and an anaerobic blood storage bag 528. OCDD 535 removes oxygen and carbon dioxide from red blood cells traveling through it. Tubing connects the various components of the blood storage system 500. Tube 512 connects collection bag 510 with OCDD 535. Tubes 518 and 520 connect OCDD 535 with blood storage bag 528. Blood storage system 500 is preferably a single-use, disposable, low cost system.

Figure 2:
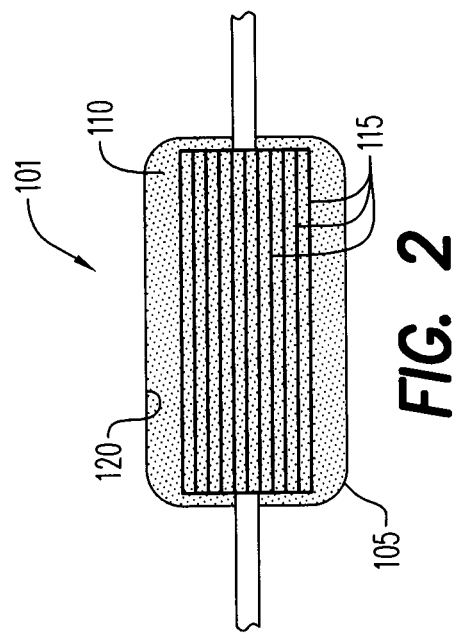
FIG. 2 illustrates a pre-storage oxygen/carbon dioxide depletion device of the present disclosure.

Referring to FIG. 2, an oxygen/carbon dioxide depletion device (OCDD) 101 contains an oxygen sorbent 110. OCDD 101 is a disposable cartridge 105 containing oxygen sorbent 110 and a series of hollow fibers 115. Oxygen sorbent 110 is a mixture of non-toxic inorganic and/or organic salts and ferrous iron or other materials with high reactivity toward oxygen. Oxygen sorbent 110 is made from particles that have significant absorbing capacity for $O_2$ (more than 5 ml $O_2$/g) and can maintain the inside of cartridge 105 to less than 0.01% which corresponds to $PO_2$ less than 0.08 mmHg. Oxygen sorbent 110 is either free or contained in an oxygen permeable envelope. OCDD 101 of the present disclosure must deplete approximately 100 mL of oxygen from a unit of blood.

After oxygen and carbon dioxide have been stripped from RBCs in the OCDD of FIG. 2, RBCs are stored in a blood storage bag 200. The oxygen content of RBC suspended in additive solution 300 must be reduced to equal to or less than 4% $SO_2$ before placing them in refrigerated storage. Further, oxygen depleted RBC must be kept in an anaerobic state and low carbon dioxide state throughout entire storage duration.

RBCs pass through an oxygen permeable film or membrane 115. The membrane or films may be constructed in a flat sheet or hollow fiber form. Films can be non porous materials that are capable of high oxygen permeability rates (polyolefins, silicones, epoxies, polyesters etc) and membrane are hydrophobic porous structures. These may be constructed of polymers (polyolefins, Teflon, PVDF, polysulfone) or inorganic materials (ceramics). Oxygen depletion takes place as RBCs pass through membrane 115. Hollow fibers may be used as a substitute for oxygen permeable films or membrane. OCDD provides a simple structure having a large surface area to remove oxygen and maintain constant flow of blood therethrough. The oxygen depletion or removal is accomplished by irreversible reaction of ferrous ion in oxygen sorbent 110 with ambient oxygen to form ferric oxide. OCDD 101 does not need agitation for oxygen removal and can be manufactured easily to withstand centrifugation as part of a blood collection system as necessary.

Referring to FIGS. 6a through 6c and FIGS. 7a through 7c, examples of flushing depletion devices are disclosed. The depletion devices function to deplete, $O_2$ and $CO_2$, or $O_2$, or $CO_2$ alone, or $O_2$ with specific levels of $CO_2$ by supplying appropriate composition of flushing gas. Gases appropriate for depletion devices are, for example, Ar, He, $N_2$, $Ar/CO_2$, or $N_2/CO_2$.

FIGS. 8a through 8c and 9a through 9c, also disclose scavenging depletion devices. Depletion takes place with the use of scavengers or sorbents and without the use of external gases. In both types of depletion devices however, carbon dioxide depletion in conjunction with oxygen depletion is effective to enhance DPG and ATP, respectively, prior to storage in blood storage bags.

Referring to FIGS. 6a through 6c, a depletion device 20 is shown. Depletion device 20 includes a plurality of fibers 25, approximately 5000 in number, through which red blood cells flow. Plurality of fibers 25 are surrounded by a plastic cylinder 30. Plastic cylinder 30 contains a gas inlet 35 and a gas outlet 40 through which a flushing gas or a combination of flushing gases, such as those mentioned above, are supplied to remove carbon and/or oxygen from blood. Specifications for depletion device 20 are shown in Table 1 below.

TABLE 1

| Prototype Specification | Eternal Gas Pathways | External Gas Pathways |
| --- | --- | --- |
| Prototype Serial #: | Device 20 | |
| Fiber Type: | Celgard 200/150-66FPI | Celgard 200/150-66FPI |
| Number of Fibers: | 5000 | 5000 |
| Active Length of Fibers (cm): | 13 | 28 |
| Fiber OD (microns): | 200 | 200 |
| Fiber ID (microns): | 150 | 150 |
| Total Length of Fibers | 15 | 30 |

TABLE 1-continued

| Prototype Specification | Eternal Gas Pathways | External Gas Pathways |
|---|---|---|
| Active Fiber Surface Area (m2): | 0.4084 | 0.8796 |

Referring to FIGS. 7a through 7c, a depletion device 45 is shown. Depletion device 45, like device 20 of FIGS. 6a to 6c, includes a plurality of fibers 50, approximately 5000 in number, through which red blood cells flow. Plurality of fibers 50 are surrounded by a plastic cylinder 55. Plastic cylinder 55 contains a gas inlet 60 and a gas outlet 65 through which a gas or a combination of gases, such as those mentioned above are supplied to remove carbon dioxide and/or oxygen from blood. Specifications for depletion device 45 are shown in Table 2 below. The active surface area of depletion of device 45 is twice that of device 20 because device 45 is twice as long as device 20.

TABLE 2

| Prototype Specification | Eternal Gas Pathways | External Gas Pathways |
|---|---|---|
| Prototype Serial #: | | Device 45 |
| Fiber Type: | Celgard 200/150-66FPI | Celgard 200/150-66FPI |
| Number of Fibers: | 5000 | 5000 |
| Active Length of Fibers (cm): | 13 | 28 |
| Fiber OD (microns): | 200 | 200 |
| Fiber ID (microns): | 150 | 150 |
| Total Length of Fibers | 15 | 30 |
| Active Fiber Surface Area (m2): | 0.4084 | 0.8796 |

FIGS. 8a through 8c disclose a depletion device 70 having a core 75 containing scavenging materials for either $O_2$, $CO_2$, or both $O_2$ and $CO_2$. Core 75 is packed by a gas permeable film with very low liquid permeability. Hollow fibers 80 are wound around core 75, and a plastic cylinder 82 contains and envelopes hollow fibers 80. In this particular embodiment, the active surface area for depletion is approximately 0.8796 $m^2$ as shown in Table 3 below.

TABLE 3

| Prototype Specification | Center Core 125 grams Sorbent | 10 individual Bundles 200 grams Sorbent |
|---|---|---|
| Prototype Serial #: | Device 70 | |
| Fiber Type: | Celgard 200/150-66FPI | Celgard 200/150-66FPI |
| Number of Fibers: | 5000 | 5000 |
| Active Length of Fibers (cm): | 13 | 28 |
| Fiber OD (microns): | 200 | 200 |
| Fiber ID (microns): | 150 | 150 |
| Total Length of Fibers | 15 | 30 |
| Active Fiber Surface Area (m2): | 0.8796 | 0.8796 |

FIGS. 9a through 9c disclose a depletion device 85 containing fiber bundles 87 enclosed in gas permeable film with very low liquid permeability. Fiber bundles 87 are surrounded by scavenging materials 89 for either $O_2$, $CO_2$ or both $O_2$ and $CO_2$. Fiber bundles 87 and scavenger materials 89 are contained within a plastic cylinder 90. The active surface area for depletion is approximately 0.8796 $m^2$ as shown in Table 4 below.

TABLE 4

| Prototype Specification | Center Core 125 grams Sorbent | 10 individual Bundles 200 grams Sorbent |
|---|---|---|
| Prototype Serial #: | | Device 85 |
| Fiber Type: | Celgard 200/150-66FPI | Celgard 200/150-66FPI |
| Number of Fibers: | 5000 | 5000 |
| Active Length of Fibers (cm): | 13 | 28 |
| Fiber OD (microns): | 200 | 200 |
| Fiber ID (microns): | 150 | 150 |
| Total Length of Fibers | 15 | 30 |
| Active Fiber Surface Area (m2): | 0.8796 | 0.8796 |

Figure 10:
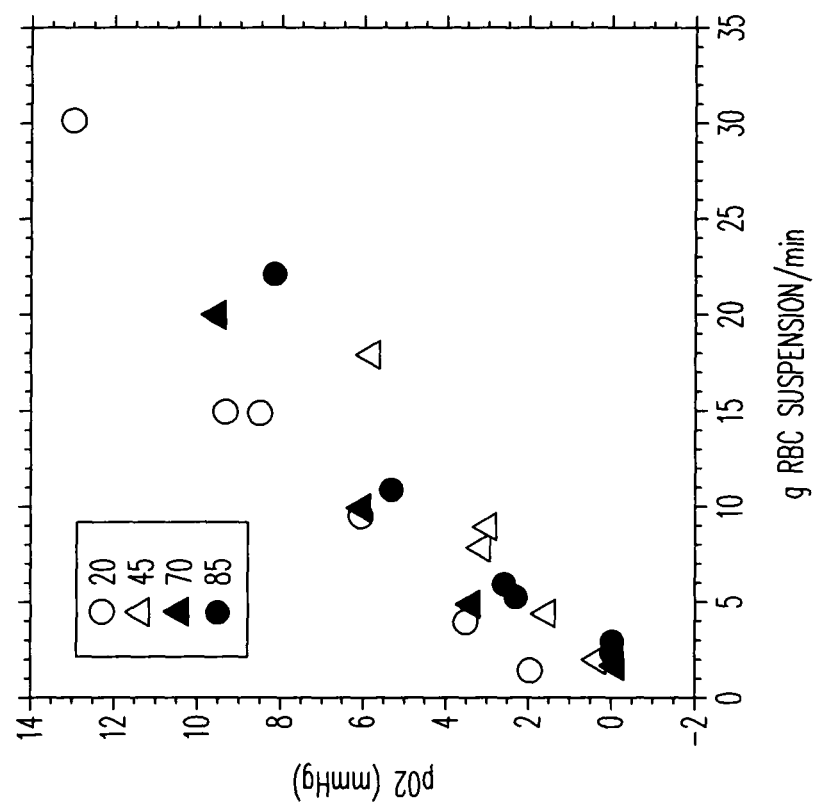
FIG. 10 illustrates a plot of flow rate of RBC suspension per minute versus oxygen partial pressure for the depletion devices of FIGS. 6a through 6c, FIGS. 7a through 7c, FIGS. 8a through 8c and FIGS. 9a through 9c.

FIG. 10 is a plot of the performance of flushing depletion devices 20 and 45 and scavenging depletion devices 70 and 85. The data of FIG. 10 was plotted using the following conditions: Hematocrit, 62% (pooled 3 units of pRBC), and 21° C. at various head heights to produce different flow rates. Oxygen/carbon dioxide scavenger (Multisorb Technologies, Buffalo, N.Y.) was activated with adding 5% and 12% w/w water vapor for device 79 and device 85, respectively. Data are plotted with flow rate (g RBC suspension per min) vs. $pO_2$ (mmHg).

In the oxygen/carbon dioxide depletion devices disclosed herein, a plurality of gas permeable films/membranes may be substituted for the plurality of hollow fibers. The films and fibers may be packed in any suitable configuration within the cartridge, such as linear or longitudinal, spiral, or coil, so long as they can receive and convey red blood cells.

FIG. 10 shows that lowest oxygen saturation is achieved using devices 45 and 85. Device 45 exhibits a larger active surface area exposed to gases along length of fibers 50. Device 85 also has a long surface area of exposure to scavenging materials. Device 85 has bundles 87 surrounded by scavenging materials 89. The space occupied by scavenging materials 89 between bundles 87 promotes dispersion of oxygen and carbon dioxide from red blood cells contained in fiber bundles 87, thus aiding scavenging of oxygen and carbon dioxide from red blood cells.

A further use of the depletion devices is to add back oxygen and or carbon dioxide prior to transfusion by flushing with pure oxygen or air. This use is for special cases, such as massive transfusions, where the capacity of the lung to re-oxygenate transfused blood is not adequate, or sickle cell anemia.

Similarly, depletion devices can be used to obtain intermediate levels or states of depletion of oxygen and carbon dioxide depending needs of the patient to obtain optimal levels in the transfused blood depending upon the patients needs.

Figure 3:
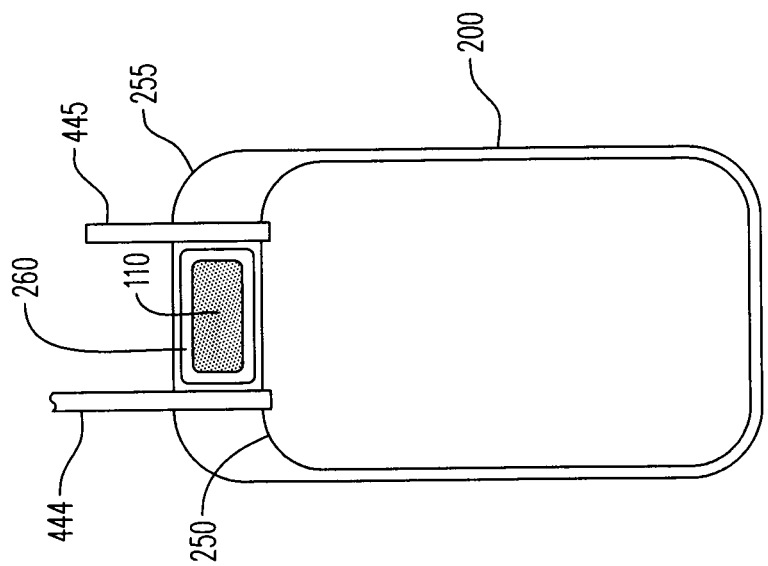
FIG. 3 illustrates a first embodiment of a blood storage bag having a storage bag with a secondary outer oxygen film containing an oxygen sorbent in a pocket.

Referring to FIG. 3, a blood storage bag 200 according to a preferred embodiment of the present disclosure is provided. Blood bag 200 has an inner blood-compatible bag 250 (preferably polyvinyl chloride (PVC)), and an outer barrier film bag 255. The material of bag 250 is compatible with RBCs. Disposed between inner bag 250 and outer oxygen barrier film bag 255 is a pocket that contains an oxygen/carbon dioxide sorbent 110. Barrier film bag 255 is laminated to the entire surface of inner bag 250. Sorbent 110 is contained in a sachet 260, which is alternately referred to as a pouch or pocket. Sorbent 110 is optimally located between tubing 440 that leads into and from bag 200, specifically between inner bag and outer oxygen barrier film bag 255. This location will ensure that oxygen disposed between these two bags will be scavenged or absorbed. Oxygen sorbent is ideally located in a pouch or pocket 260 and not in contact with RBCs. Oxygen sorbent may also be combined with $CO_2$ scavengers or sorbents, enabling sorbent 110 to deplete both oxygen and carbon dioxide at the same time.

Referring to FIGS. 4a and 4b, blood storage bags 201 and 202 are configured to store RBCs for extended storage periods of time. Inner blood storage bags 205 are preferably made from DEHP-plasticized PVC and are in contact with RBCs. DEHP-plasticized PVC is approximately 200 fold less permeable to oxygen compared to silicone. However, PVC is insufficient as an oxygen barrier to maintain the anaerobic state of RBCs throughout the storage duration. Therefore, blood storage bags 201 and 202 are fabricated with outer transparent oxygen barrier film 206 (e.g. nylon polymer) laminated to the outer surface inner blood bag 205. This approach, as well as one shown in FIG. 3, uses accepted PVC for blood contact surface (supplying DEHP for cell stabilization) at the same time prevents oxygen entry into the bag during extended storage.

In FIG. 4a, a small sachet 210 containing oxygen/carbon dioxide sorbent 110 enveloped in oxygen-permeable, RBC compatible membrane is enclosed inside of laminated PVC bag 205 and in contact with RBCs. Small sachet envelope 210 is preferably made from a silicone or siloxane material with high oxygen permeability of biocompatible material. Sachet envelope 210 has a wall thickness of less than 0.13 mm thickness ensures that $O_2$ permeability ceases to become the rate-limiting step. PVC bag 205 may also contain carbon dioxide scavengers.

Referring to FIG. 4b, bag 202 has a similar configuration to bag 201 of FIG. 4a. However, bag 202 has a large sorbent 215 enclosed inside of PVC bag 205. Large sorbent 215 preferably has a comb-like configuration to rapidly absorb oxygen during extended storage. The benefit of laminated bags of FIGS. 4a and 4b is that once RBCs are anaerobically stored in bags, no further special handling is required. Similarly, bag 202 may contain carbon dioxide scavenger to provide carbon dioxide-scavenging in addition to oxygen-scavenging capability.

Figure 5B:
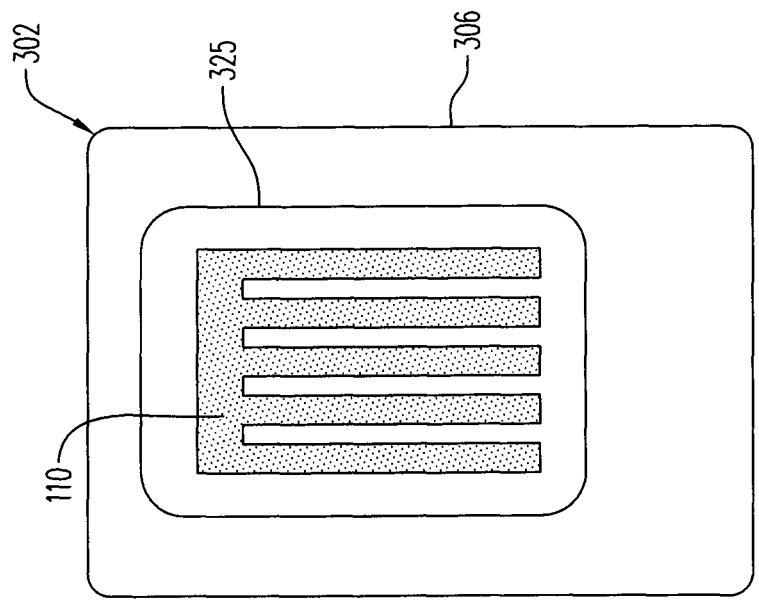
FIG. 5b illustrates a fifth embodiment of a blood storage bag having a secondary outer barrier bag surrounding an inner blood storage bag having a large oxygen sorbent sachet enclosed in a gas permeable, red blood cell compatible polymers in contact with RBCs.
Figure 5A:
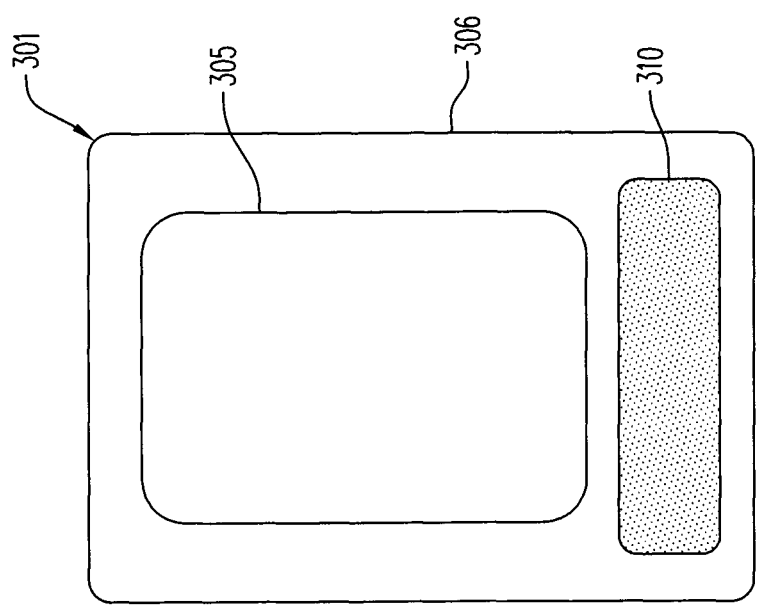
FIG. 5a illustrates a fourth embodiment of a blood storage bag having a secondary configured secondary outer barrier bag surrounding an inner blood storage bag having an oxygen sorbent.

Referring to the embodiments of FIGS. 5a and 5b, RBCs are stored in secondary bags 301 and 302, respectively, in order to maintain an anaerobic storage environment for RBC storage. Secondary bags 301 and 302 are transparent oxygen barrier films (e.g., nylon polymer) that compensate for the inability of PVC blood bags 305 and 320, respectively, to operate as a sufficient oxygen barrier to maintain RBCs in an anaerobic state. Secondary bags 301 and 302 are made with an oxygen barrier film, preferably a nylon polymer or other transparent, flexible film with low oxygen permeability.

Referring to FIG. 5a, a small oxygen/carbon dioxide sorbent 310 is disposed between a PVC barrier bag 305 and secondary bag 306 to remove slowly diffusing oxygen. FIG. 5a is similar to the preferred embodiment of the blood bag of FIG. 3 except that secondary bag 306 is separate from and not bonded to bag 305 in this embodiment. PVC bag 305 including ports are enclosed in secondary barrier bag 305. Oxygen sorbent 310 may optionally contain carbon dioxide scavengers to provide both oxygen and carbon dioxide scavenging capability.

Referring to FIG. 5b, a secondary bag 302 contains a large sachet 325 inside of PVC bag 320. Sachet 325 is filled with oxygen/carbon dioxide sorbent 110. Sachet 325 is a molded element with surface texture to increase the surface area. Sachet 325 has a comb-like geometry for rapid oxygen/carbon dioxide depletion. Sachet 325 acts rapidly to strip oxygen/carbon dioxide from RBCs prior to refrigeration and storage of RBCs in place of OCDD of FIG. 2. However, with this configuration, agitation is necessary, therefore sachet 325 must possess a large surface area, high oxygen/carbon dioxide permeability and mechanical strength to withstand centrifugation step during component preparation and the prolonged storage. Sachet 325 is preferably made from materials such as 0.15 mm thick silicone membrane with surface texture to increase the surface area. Sachet 325 may be made from materials such as PTFE or other fluoropolymer. Sachet 325 may have a rectangular shape such, such as, for example, a 4"×6" rectangle, although other sizes are possible, for the anaerobic maintenance. Sachet 325 may contain carbon dioxide scavengers in addition to oxygen scavengers to provide oxygen and carbon dioxide scavenging capability.

The embodiments of FIGS. 5a and 5b are easily made from off-shelf components except for sachet 325 of FIG. 5b. In order to access RBCs for any testing, secondary bags 301 and 302 must be opened. Unless the unit is transfused within short time, RBC must be re-sealed with fresh sorbent for further storage. (1 day air exposure of storage bag would not oxygenate blood to appreciable degree, since PVC plasticized with DEHP has relatively low permeability to oxygen).

In FIGS. 4a, 4b, 5a and 5b, the PVC bag is preferably formed with the oxygen barrier film, such as an $SiO_2$ layer formed with the sol-gel method. A portion of the sheet material will be sealed on standard heat sealing equipment, such as radiofrequency sealers. Materials options may be obtained in extruded sheets and each tested for oxygen barrier, lamination integrity, and seal strength/integrity.

For each of the several embodiments addressed above, an additive solution from bag 300 is provided prior to stripping oxygen and carbon dioxide from the RBCs is used. The additive solution 300 preferably contains the following composition adenine 2 mmol/L; glucose 110 mmol/L; mannitol 55 mmol/L; NaCl 26 mmol/L; $Na_2HPO_4$ 12 mmol/L citric acid and a pH of 6.5. Additive solution 300 is preferably an acidic additive solution OFAS3, although other similar additive solutions could also be used that are shown to enhance oxygen/carbon dioxide-depleted storage. OFAS3 has shown enhanced ATP levels and good in vivo recovery as disclosed herein. While OFAS3 is a preferred additive solution, other solutions that offer similar functionality could also be used. Alternatively, additive solutions used currently in the field, such as AS1, AS3, AS5, SAGM, and MAPS can also be used. Additive solutions help to prevent rapid deterioration of RBCs during storage and are typically added prior to RBCs being made anaerobic.

Additionally, we envision that the OCDD and storage bags 100 and 200 can be manufactured independent of other components of the disposable, anaerobic blood storage system (i.e., every item upstream of and including leukoreduction filter 400 in FIG. 1).

It is within the scope of the present disclosure to remove oxygen from the RBCs or to strip oxygen and carbon dioxide from the blood prior to storage in the storage bags. An oxygen scavenger can be used to remove the oxygen from the RBCs prior to storage in the blood bags. As used herein, "oxygen scavenger" is a material that irreversibly binds to or combines with oxygen under the conditions of use. For example, the oxygen can chemically react with some component of the material and be converted into another compound. Any material where the off-rate of bound oxygen is zero can serve as an oxygen scavenger. Examples of oxygen scavengers include iron powders and organic compounds. The term "oxygen sorbent" may be used interchangeably herein with oxygen scavenger. As used herein, "carbon dioxide scavenger" is a material that irreversibly binds to or combines with carbon dioxide under the conditions of use. For example, the carbon dioxide can chemically react with some component of the material and be converted into another compound. Any material where the off-rate of bound carbon dioxide is zero can serve as a carbon dioxide scavenger. The term "carbon dioxide sorbent" may be used interchangeably herein with carbon dioxide scavenger. For example, oxygen scavengers and carbon dioxide scavengers are provided by Multisorb Technologies (Buffalo, N.Y.). Oxygen scavengers may exhibit a secondary functionality of carbon dioxide scavenging. Such materials can be blended to a desired ratio to achieve desired results.

Carbon dioxide scavengers include metal oxides and metal hydroxides. Metal oxides react with water to produce metal hydroxides. The metal hydroxide reacts with carbon dioxide to form water and a metal carbonate. For example, if calcium oxide is used, the calcium oxide will react with water that is added to the sorbent to produce calcium hydroxide $$CaO+H_2O \rightarrow Ca(OH)_2$$

The calcium hydroxide will react with carbon dioxide to form calcium carbonate and water.

$$Ca(OH)_2+CO_2 \rightarrow CaCO_3+H_2O$$

It will be appreciated that scavengers can be incorporated into storage receptacles and bags in any known form, such as in sachets, patches, coatings, pockets, and packets.

If oxygen removal is completed prior to introduction of the RBCs to the blood storage device, then it can be accomplished by any method known in the art. For example, a suspension of RBCs can be repeatedly flushed with an inert gas (with or without a defined concentration of carbon dioxide), with or without gentle mixing, until the desired oxygen and or carbon dioxide content is reached or until substantially all of the oxygen and carbon dioxide has been removed. The inert gas can be argon, helium, nitrogen, mixtures thereof, or any other gas that does not bind to the hememoiety of hemoglobin.

The OCDDs and various storage bags of the present disclosure can be used in varying combinations. For example, OCDD 101 of FIG. 2 can be used with blood bag of FIG. 3, 201 of FIG. 4a or 301 of FIG. 5a. When oxygen is depleted by in-bag sachet 215 of FIG. 5b, it can be stored as in FIG. 5b or oxygen/carbon dioxide-depleted content transferred to the final storage bag such as FIG. 3, FIG. 4a or FIG. 5a for extended storage. Other combinations and configurations are fully within the scope of the present disclosure.

The present disclosure also provides another embodiment of a blood storage device. The device is a sealed receptacle adapted to retain and store red blood cells. The receptacle has walls formed from a laminate. The laminate has (a) an outer layer of a material substantially impermeable to oxygen and carbon dioxide, (b) an inner layer of a material compatible with red blood cells, and (c) an interstitial layer between the outer layer and the inner layer. The interstitial layer is of a material having admixed therein an amount of either or both of an oxygen scavenger and a carbon dioxide scavenger. The layers preferably take the form of polymers. A preferred polymer for the outer layer is nylon. A preferred polymer for inner layer is PVC. The polymer of the interstitial layer should provide effective adhesion between the inner and outer layers and provide effective admixture of oxygen scavengers and/or carbon dioxide scavengers therein. Useful polymers for the interstitial layer include, for example, olefin polymers, such as ethylene and propylene homopolymers and copolymers, and acrylic polymers.

The present disclosure also provides another embodiment of a blood storage system. The system has a collection bag for red blood cells; a unitary device for depleting oxygen and carbon dioxide and reducing leukocytes and/or platelets from red blood cells; a storage bag for red blood cells; and tubing connecting the collection bag to the unitary device and the unitary device to the storage bag. A feature of this embodiment is that the functions of depleting oxygen and carbon dioxide and reducing leukocytes and/or platelets from red blood cells are combined into a single, unitary device rather than require separate devices. For instance, unitary device can take the form of a single cartridge. Leukocyte and/or platelet reduction is typically carried out by passing red blood cells through a mesh. In this embodiment, a mesh can be incorporated into either the flushing or the scavenging oxygen/carbon dioxide depletion device disclosed herein. The mesh is preferably located within the device so that leukocyte and/or platelet reduction takes place prior to the onset of flushing or scavenging.

The following are examples of the present disclosure and are not to be construed as limiting.

EXAMPLES

The eight graphs below show the results of a 3-arm study showing: a control (aerobic OFAS3 with no $O_2$ or $CO_2$ depletion), anaerobic OFAS3 (both $O_2$ and $CO_2$ depleted with pure Ar), and $O_2$ only depleted with 95% Ar and 5% $CO_2$ ($CO_2$ is not depleted).

Whole blood was collected into CP2D (Pall), centrifuged 2K×G for 3 minutes, plasma removed, and additive solution AS-3 (Nutricel, Pall), or experimental OFAS3 added. The unit was evenly divided into 3 600 mL bags. 2 bags were gas exchanged ×7 with Ar or Ar/$CO_2$, transferred to 150 mL PVC bags and stored 1° C. to 6° C. in anaerobic cylinders with Ar/$H_2$ or Ar/$H_2$/$CO_2$. One control bag was treated in the same manner without a gas exchange and stored 1° C. to 6° C. in ambient air. Bags were sampled weekly for up to 9 weeks.

The plots of FIGS. 11a, 11c, 11e and 11g: use the additive solution OFAS3 (200 mL; experimental, proprietary) and the plots of FIGS. 11b, 11d, 11f and 11h, use the AS-3 additive solution. Comparing additive solutions, effects of $CO_2$ depletion on DPG levels were similar. OFAS3 showed higher ATP when oxygen was depleted (±$CO_2$), and $O_2$ depletion alone showed significant enhancement of ATP compared to aerobic control. AS-3 additive exhibited no significant enhancement of ATP when $O_2$ alone was depleted.

Figure 11B:
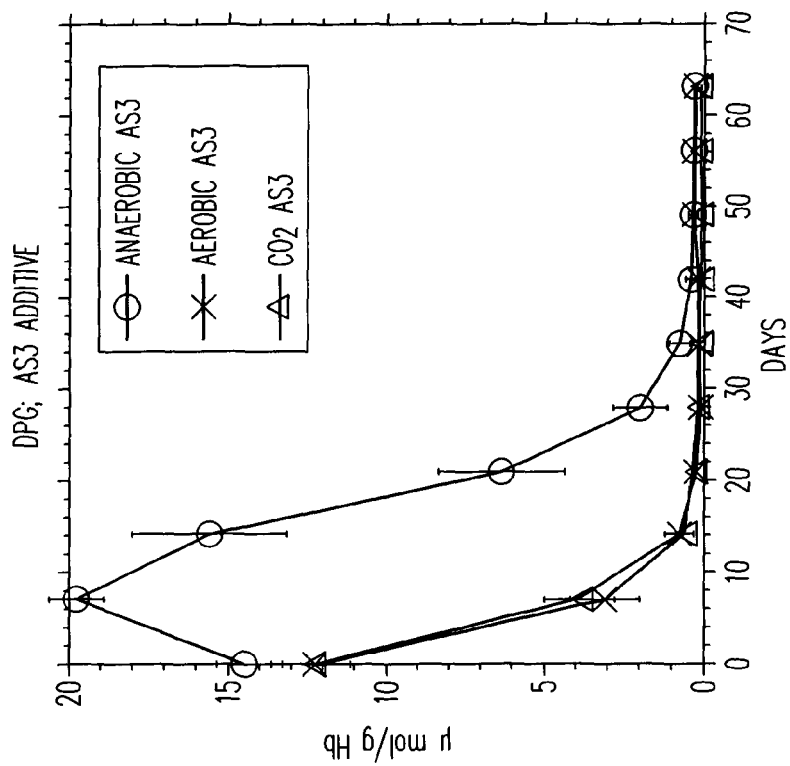
FIGS. 11a through 11h illustrate plots of the effect of oxygen and oxygen and carbon dioxide depletion on metabolic status of red blood cells during refrigerated storage.
Figure 11A:
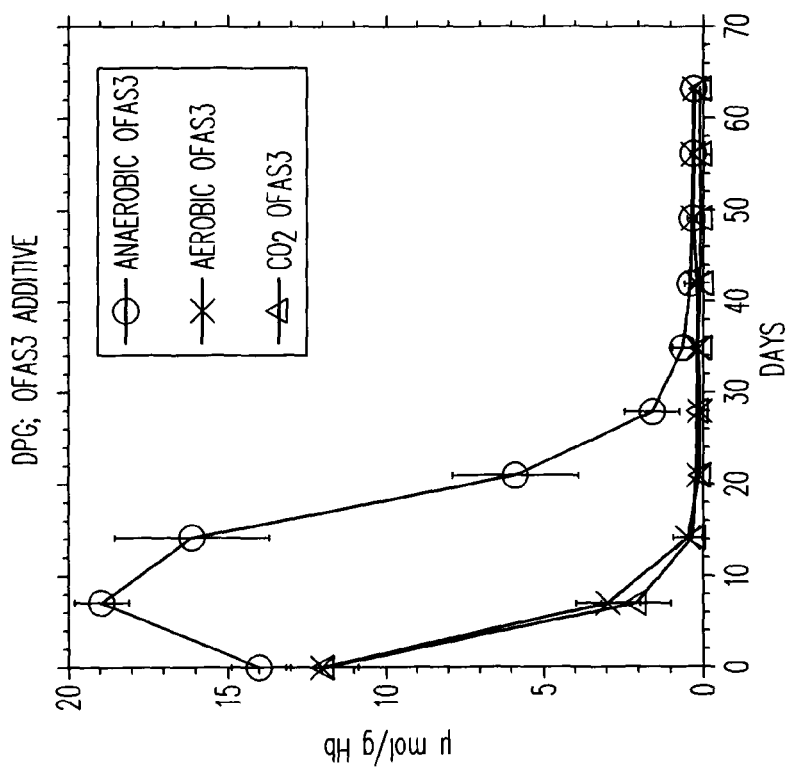

FIGS. 11a and 11b: DPG levels during storage. DPG levels were maintained for over 2 weeks, when $CO_2$ was removed in addition to oxygen.

Figure 11D:
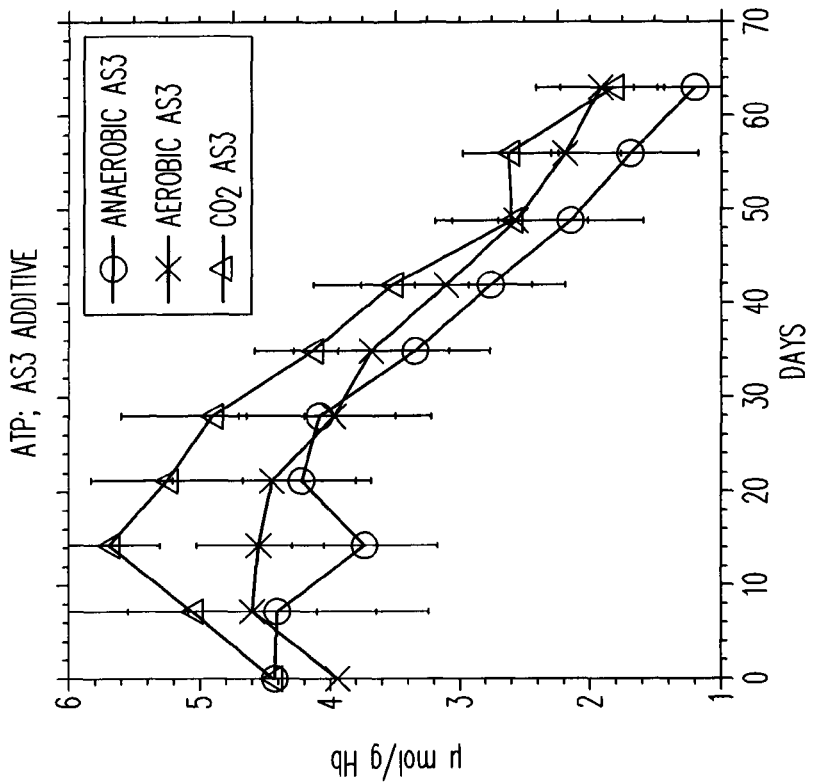
Figure 11C:
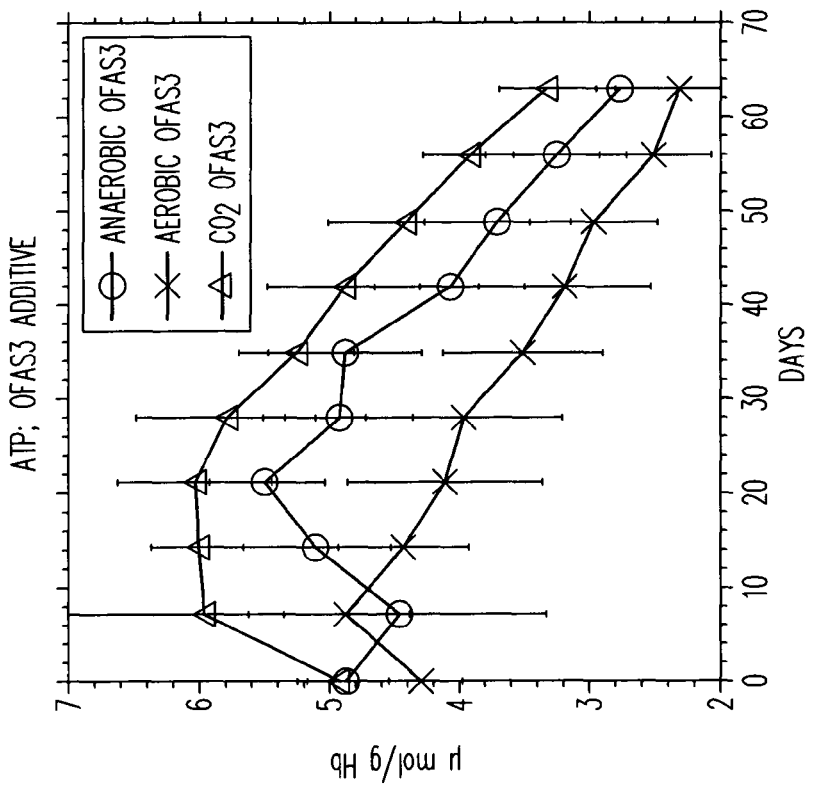

FIG. 11c: ATP levels during storage with OFAS3. Highest ATP levels were achieved with OFAS3 RBC when $O_2$ only was depleted. For $O_2$/$CO_2$ depletion, intermediate levels of ATP were observed compared to the control while very high DPG levels were attained during first 2.5 weeks. Very high levels of ATP may suggest higher rate of 24-hour post transfusion recovery. Therefore, extent of carbon dioxide and oxygen depletion levels may be adjusted to meet the specific requirement of the recipient. DPG levels can be maintained very high (at the expense of ATP) for purposes of meeting acute oxygen demand of recipient. Conversely, very high ATP levels may allow higher 24-hour recovery rate (lower fraction of non-viable RBC upon transfusion) thereby reducing the quantity of blood needed to be transfused (up to 25% of RBC are non-viable). More importantly, this would benefit chronically transfused patients who may not demand highest oxygen transport efficiency immediately after transfusion (DPG level recovers in body after 8-48 hours) who suffers from toxic iron overloading caused by non-viable RBCs.

FIG. 11d: ATP levels during storage with AS3. Highest ATP levels were achieved with AS3 RBC when $O_2$ only was depleted. No significant differences in ATP levels where observed with control and $O_2$ depletion alone.

Figure 11F:
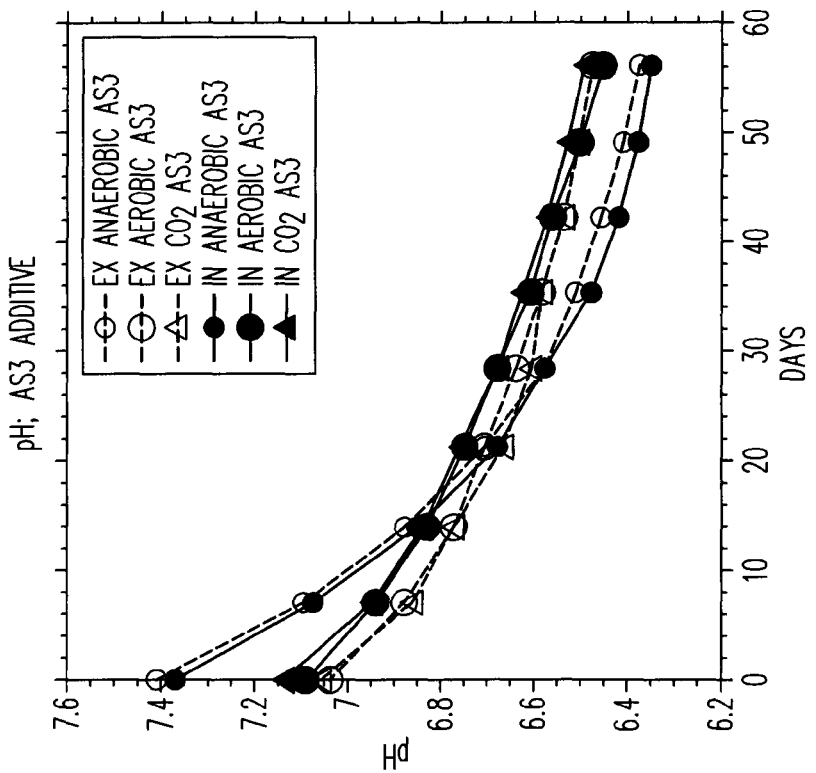
Figure 11E:
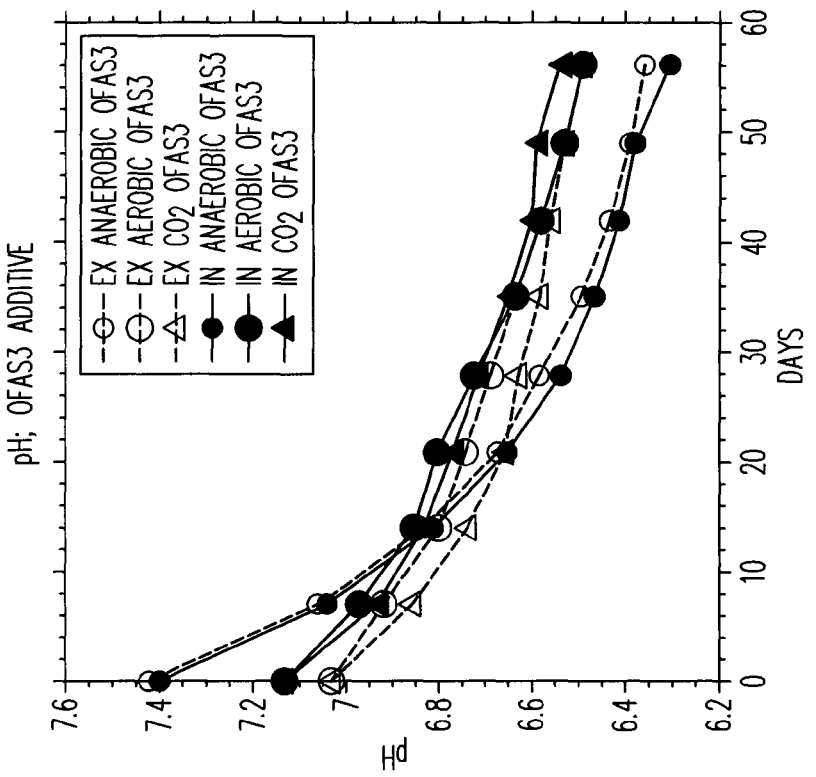

FIGS. 11e and 11f: pH of RBC cytosol (in) and suspending medium (ex). Immediately after gas exchange (day 0), significant rise in pH (in and ex) was observed only when $CO_2$ was depleted together with $O_2$. Rapid rates of pH decline observed with $CO_2/O_2$ depleted samples were caused by higher rates of lactate production (FIGS. 11g and 11h).

Figures 11G, 11H:
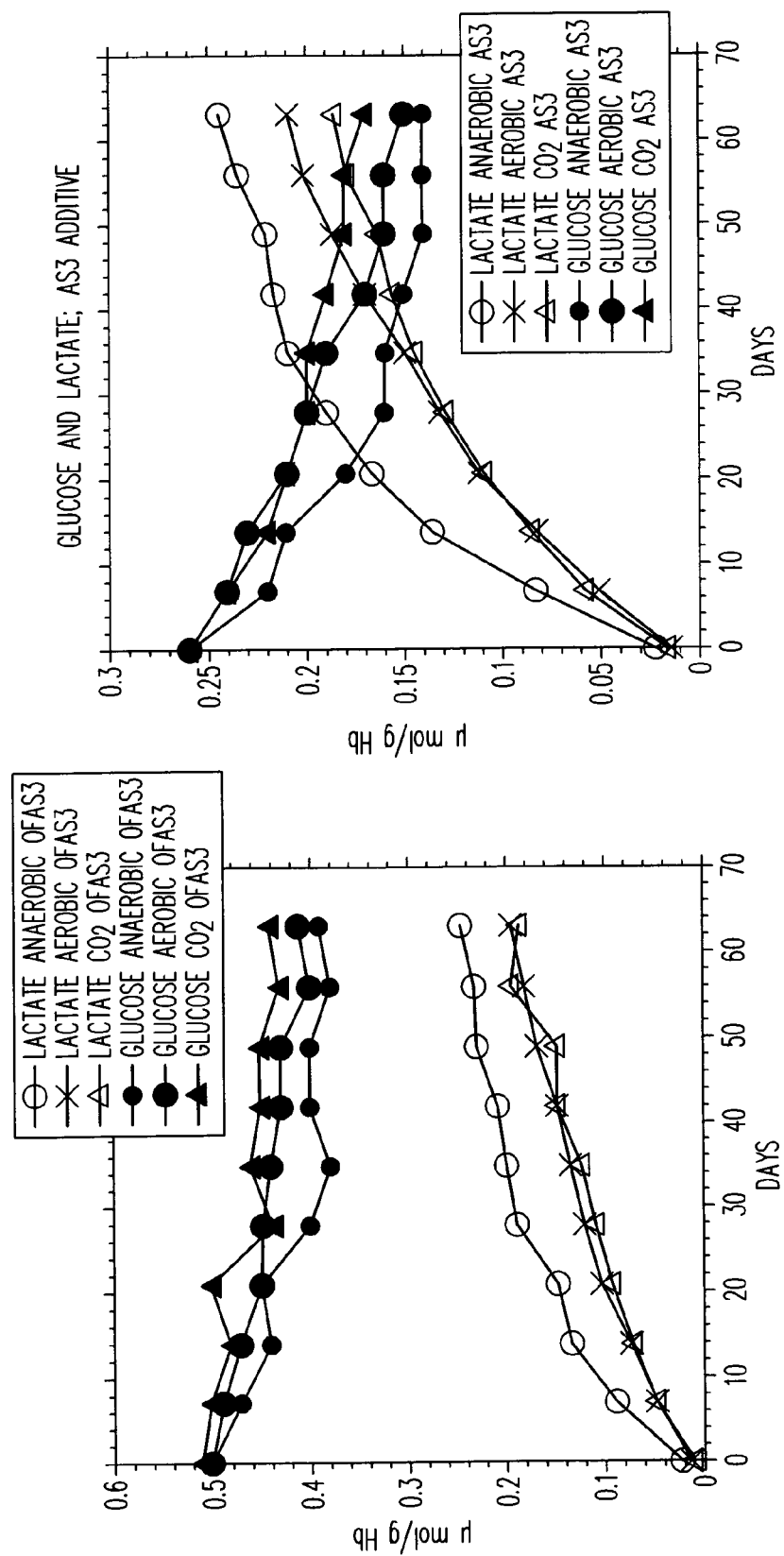

FIGS. 11g and 11h: Normalized (to hemoglobin) glucose and lactate levels during storage with OFAS3 and AS3. Higher rates of glucose depletion and lactate productions correspond to high DPG levels observed in panels A and B. Legends for symbols/lines are same for both panels. OFAS3 additive contains similar glucose concentration with ×2 volume resulting in higher normalized glucose levels.

FIGS. 11a and 11c taken together, suggest that extent of increases (compared to control) of ATP and DPG levels may be adjusted by controlling level of $CO_2$ depletion, when $O_2$ is depleted. Higher glucose utilization and lactate production were observed with enhanced DPG production (FIG. 11g). This may be also effective with AS3 additive, since similar trend in glucose utilization and lactate production were observed (FIG. 11h).

Although the present disclosure describes in detail certain embodiments, it is understood that variations and modifications exist known to those skilled in the art that are within the disclosure. Accordingly, the present disclosure is intended to encompass all such alternatives, modifications and variations that are within the scope of the disclosure as set forth in the disclosure.

What is claimed is:

1. A method for removing oxygen from red blood cells, comprising:
   passing red blood cells through an oxygen depletion device, wherein said depletion device comprises:
   a receptacle of a solid material having an inlet and an outlet adapted to receiving and expelling a flushing gas; and
   a plurality of gas-permeable films or membranes extending within said receptacle from an entrance to an exit thereof, wherein said plurality of gas-permeable films or membranes are formed of a material permeable to oxygen and are adapted to receiving and conveying said red blood cells,
   wherein said plurality of gas-permeable films or membranes are each constructed in a flat sheet, and wherein said flushing gas comprises 5% $CO_2$.

2. The blood storage system comprising,
   a collection bag for red blood cells;
   an oxygen depletion device;
   an oxygen impermeable storage bag for red blood cells; and
   tubing connecting said collection bag to said oxygen depletion device and tubing connecting said oxygen depletion device to said oxygen impermeable storage bag,
   wherein said oxygen depletion device comprises:
   a) a cartridge;
      a plurality of gas-permeable films or membranes formed of a material permeable to oxygen and are adapted to receiving and conveying red blood cells extending within said cartridge from an entrance to an exit thereof; and
      an amount of an oxygen scavenger packed within said cartridge and contiguous to and in between said plurality of gas-permeable films or membranes; or,
   b) a receptacle of a solid material having an inlet and an outlet adapted to receiving and expelling a flushing gas; and
      a plurality of gas-permeable films or membranes formed of a material permeable to oxygen and are adapted to receiving and conveying red blood cells extending within said receptacle from an entrance to an exit thereof,
   wherein said plurality of gas-permeable films or membranes are each constructed in a flat sheet, and wherein said oxygen impermeable storage bag for red blood cells has an inner blood-compatible surface comprising di-2-ethylhexyl phthalate (DEHP) plasticized polyvinyl-chloride (PVC).

3. A blood storage system comprising:
   a collection bag for red blood cells;
   a unitary device for depleting oxygen and reducing leukocytes from red blood cells;
   an oxygen impermeable storage bag for red blood cells; and
   tubing connecting the collection bag to said unitary device and tubing connecting said unitary device to said oxygen impermeable storage bag.

4. The blood storage system of claim 3, wherein said unitary device further comprises platelet depletion.

5. The blood storage system of claim 3, wherein said oxygen impermeable storage bag for red blood cells has an inner blood-compatible surface comprising di-2-ethylhexyl phthalate (DEHP) plasticized polyvinyl-chloride (PVC).

6. The blood storage system of claim 3, wherein said oxygen impermeable storage bag for red blood cells has an inner blood-compatible surface without di-2-ethylhexyl phthalate (DEHP).

7. A method for increasing adenosine triphosphate (ATP) levels in red blood cells, comprising: mixing red blood cells with an acidic additive solution, and passing said red blood cells through an oxygen depletion device,
   wherein said oxygen depletion device comprises:
   a) a cartridge;
      a plurality of gas-permeable films or membranes, extending within said cartridge from an entrance to an exit thereof, formed of a material permeable to oxygen and adapted to receiving and conveying said red blood cells; and
      an amount of an oxygen scavenger packed within said cartridge and contiguous to and in between said plurality of gas-permeable films or membranes; or,
   b) a receptacle of a solid material having an inlet and an outlet adapted to receiving and expelling a flushing gas; and
      a plurality of gas-permeable films or membranes formed of a material permeable to oxygen and are adapted to receiving and conveying said red blood cells extending within said receptacle from an entrance to an exit thereof,
   wherein said plurality of gas-permeable films or membranes are each constructed in a flat sheet.

8. The method of claim 7, wherein said oxygen depletion device depletes oxygen in said red blood cells to less than, or equal to, 4% oxygen saturation ($SO_2$).

* * * * *